United States Patent
Plumptre

(10) Patent No.: US 11,291,776 B2
(45) Date of Patent: Apr. 5, 2022

(54) CAP ASSEMBLY FOR A DRUG DELIVERY DEVICE AND METHOD FOR ASSEMBLING A CAP ASSEMBLY

(71) Applicant: Sanofi-Aventis Deutschland GMBH, Frankfurt am Main (DE)

(72) Inventor: David Aubrey Plumptre, Warwick (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 312 days.

(21) Appl. No.: 16/303,458

(22) PCT Filed: May 29, 2017

(86) PCT No.: PCT/EP2017/062924
§ 371 (c)(1),
(2) Date: Nov. 20, 2018

(87) PCT Pub. No.: WO2017/207504
PCT Pub. Date: Dec. 7, 2017

(65) Prior Publication Data
US 2020/0316308 A1    Oct. 8, 2020

(30) Foreign Application Priority Data
May 31, 2016    (EP) .................................. 16172154

(51) Int. Cl.
*A61M 5/00*    (2006.01)
*A61M 5/32*    (2006.01)
*A61M 5/31*    (2006.01)

(52) U.S. Cl.
CPC ........ *A61M 5/3202* (2013.01); *A61M 5/3213* (2013.01); *A61M 2005/3104* (2013.01); *A61M 2205/02* (2013.01); *A61M 2207/00* (2013.01)

(58) Field of Classification Search
CPC .. A61M 2005/3104; A61M 2005/3109; A61M 2005/312; A61M 2005/3201;
(Continued)

(56) References Cited

U.S. PATENT DOCUMENTS 2,230,455 A    2/1941    Githens
2,320,455 A *  6/1943    Feig .................... B43K 25/022
                                                    24/11 P
(Continued)

FOREIGN PATENT DOCUMENTS

CA    2813130    4/2012
CN    87208812   4/1988
(Continued)

OTHER PUBLICATIONS

International Preliminary Report on Patentability in Application No. PCT/EP2017/062924, dated Dec. 4, 2018, 7 pages.
(Continued)

*Primary Examiner* — Rebecca E Eisenberg
(74) *Attorney, Agent, or Firm* — Fish & Richardson P.C.

(57) ABSTRACT

A cap assembly for a drug delivery device is described comprising a cap, and a clip element which is configured to be attached to the cap, the clip element comprising a first component, and a second component, wherein the first component is at least partly received by the second component, wherein the first component and the second component are firmly connected to one another, and wherein the connection between the first component and the second component is the means by which the second component is attached to the cap. Moreover, a method for assembling a cap assembly is described.

20 Claims, 18 Drawing Sheets

(58) Field of Classification Search
CPC .. A61M 5/3202; A61M 5/3213; A61M 5/002; B65D 2583/045; B65D 51/18; B43K 25/022
See application file for complete search history.

(56) References Cited

U.S. PATENT DOCUMENTS

| | | | | |
|---|---|---|---|---|
| 4,765,767 | A * | 8/1988 | Marynissen | B43K 23/126 24/11 F |
| 5,480,387 | A * | 1/1996 | Gabriel | A61M 5/20 604/134 |
| 5,730,720 | A * | 3/1998 | Sites | A61M 1/369 604/27 |
| 5,730,723 | A * | 3/1998 | Castellano | A61M 5/30 604/143 |
| 6,479,737 | B1 * | 11/2002 | Lebeda | G10D 13/12 84/422.4 |
| 2004/0052471 | A1 | 3/2004 | Furukawa et al. | |
| 2004/0052571 | A1 | 3/2004 | Furukawa et al. | |
| 2010/0272499 | A1 * | 10/2010 | Wysocan | B43K 8/024 401/221 |
| 2014/0323976 | A1 * | 10/2014 | Jugl | A61M 5/3213 604/197 |
| 2015/0050064 | A1 * | 2/2015 | Rolion | B43K 25/024 401/131 |

FOREIGN PATENT DOCUMENTS

| | | |
|---|---|---|
| CN | 2542451 | 4/2003 |
| CN | 2700120 | 5/2005 |
| CN | 201633354 | 11/2010 |
| CN | 103085537 | 5/2013 |
| CN | 202911359 | 5/2013 |
| CN | 105492046 | 4/2016 |
| CN | 105492049 | 4/2016 |
| CN | 105492050 | 4/2016 |
| JP | S60-123282 | 8/1985 |
| JP | S63-500650 | 3/1988 |
| JP | 2006-192576 | 7/2006 |
| JP | 2008-246754 | 10/2008 |
| JP | 2012-025077 | 2/2012 |
| JP | 2016-529012 | 9/2016 |
| JP | 2016-531682 | 10/2016 |
| RU | 2136321 | 9/1999 |
| TW | 201026350 | 7/2010 |
| WO | WO 1987/000799 | 2/1987 |
| WO | WO 95/08358 | 3/1995 |
| WO | WO 2004/052571 | 6/2004 |
| WO | WO 2006/032385 | 3/2006 |
| WO | WO 2010/063704 | 6/2010 |
| WO | WO 2010/142813 | 12/2010 |
| WO | WO 2012/001493 | 1/2012 |
| WO | WO 2015/028439 | 3/2015 |
| WO | WO 2015/028440 | 3/2015 |
| WO | WO 2015/028441 | 3/2015 |

OTHER PUBLICATIONS

International Search Report and Written Opinion in Application No. PCT/EP2017/062924, dated Jul. 12, 2017, 11 pages.

* cited by examiner

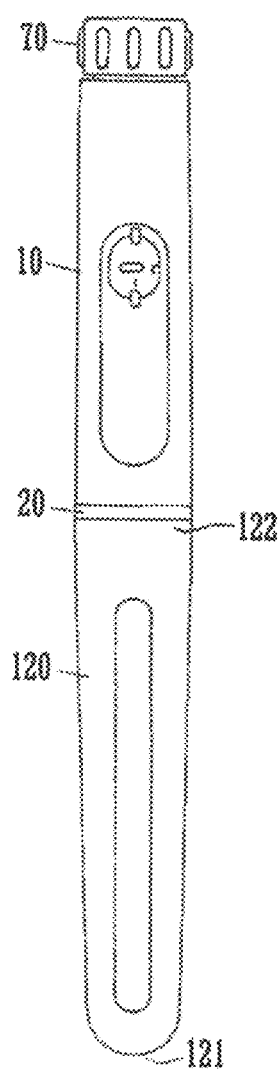
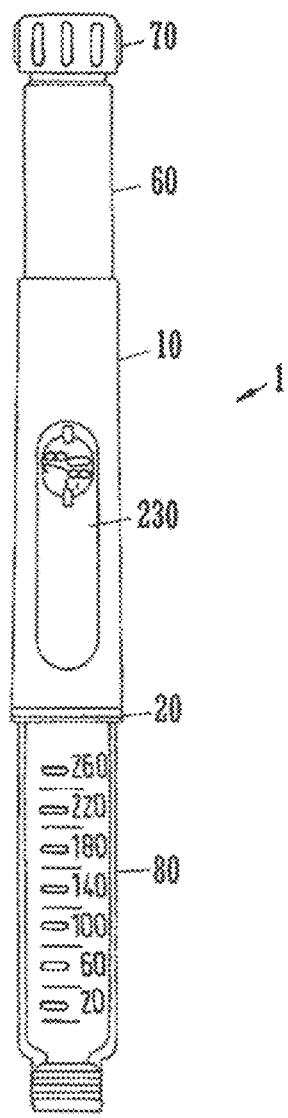

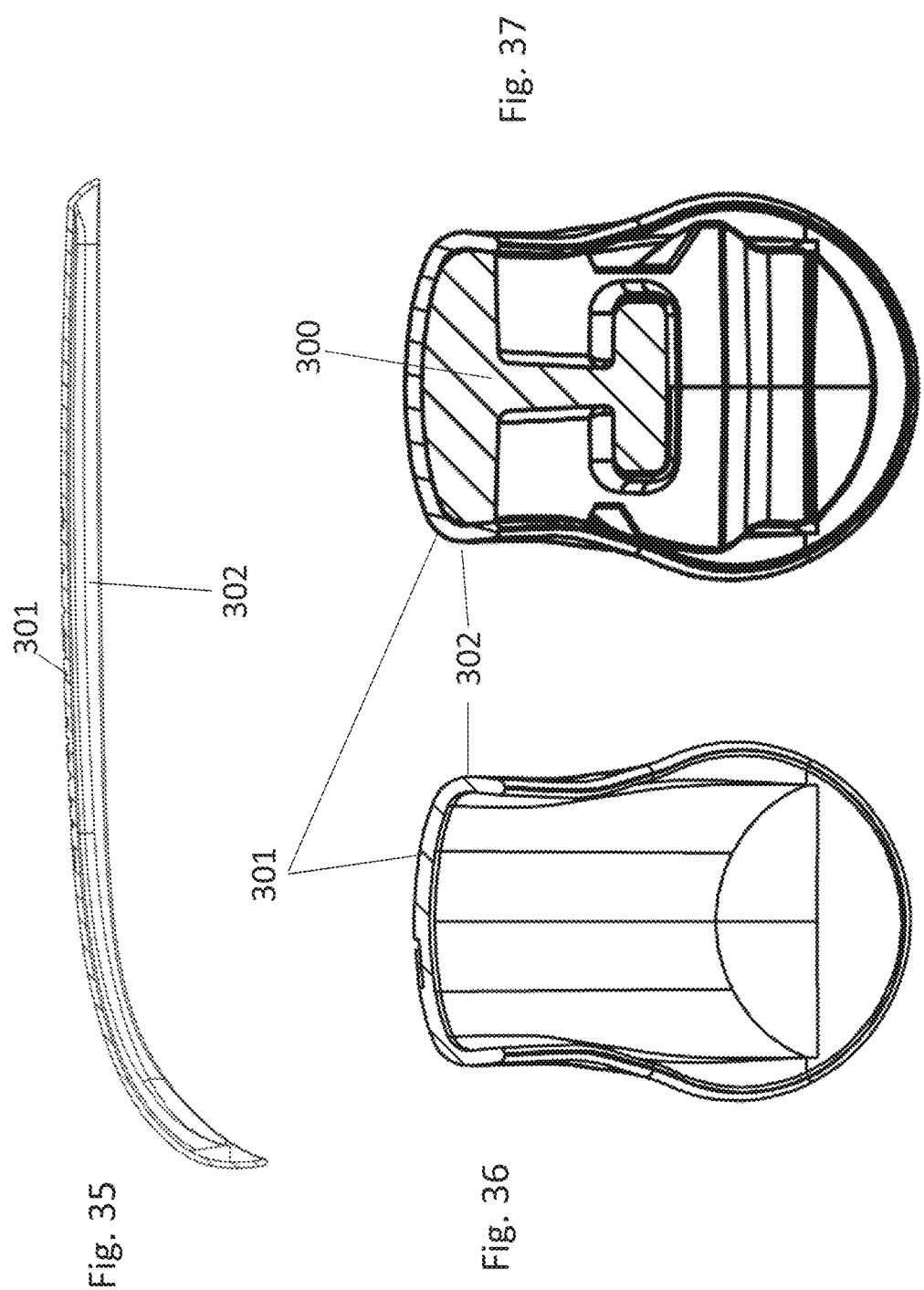

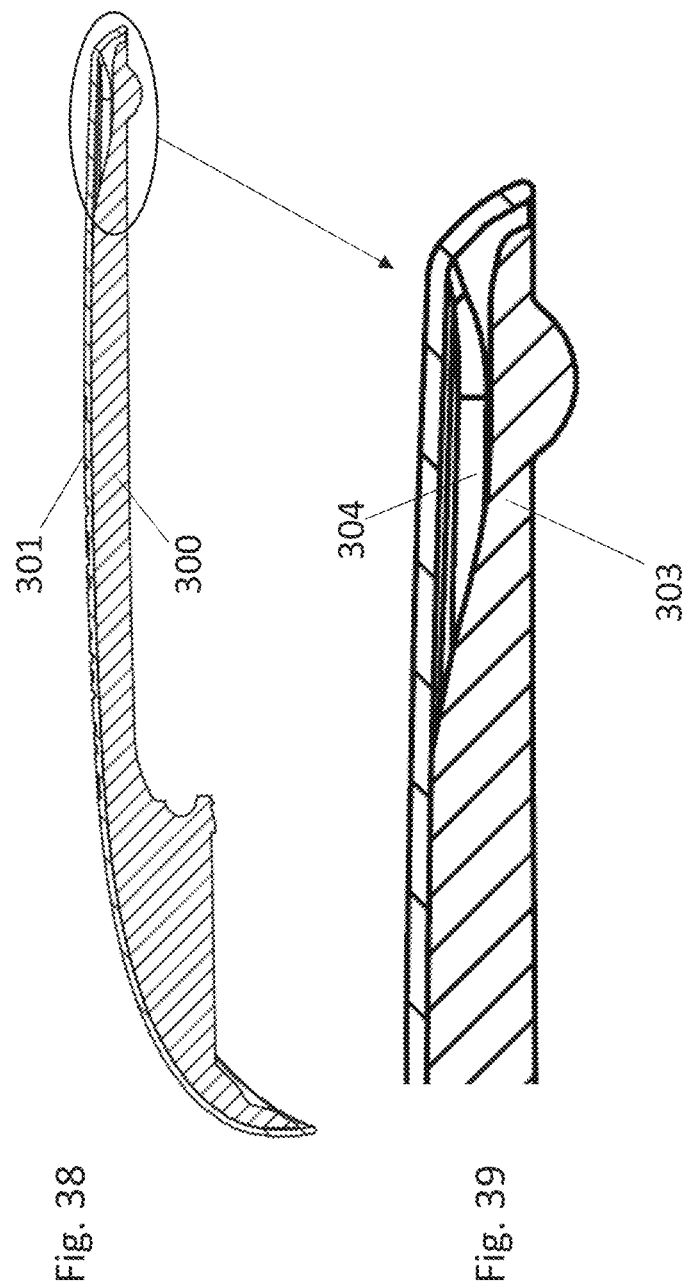

CAP ASSEMBLY FOR A DRUG DELIVERY DEVICE AND METHOD FOR ASSEMBLING A CAP ASSEMBLY

CROSS REFERENCE TO RELATED APPLICATIONS

The present application is the national stage entry of International Patent Application No. PCT/EP2017/062924, filed on May 29, 2017, and claims priority to Application No. EP 16172154.3, filed on May 31, 2016, the disclosures of which are incorporated herein by reference.

TECHNICAL FIELD

The present disclosure relates to a cap assembly for a drug delivery device. Furthermore, the present disclosure relates to a method for assembling a cap assembly.

BACKGROUND

Drug delivery devices, in particular pen-type drug delivery devices, have application where regular injection by persons without formal medical training occurs. This may be increasingly common among patients having diabetes where self-treatment enables such patients to conduct effective management of their disease. In practice, such a drug delivery device allows a user to dispense a number of user-variable doses or fixed doses of a medicament.

There are fundamentally two types of drug delivery devices: resettable (i.e. reusable) devices and non-resettable (i.e. disposable) devices. For example, disposable drug delivery devices do not have removable pre-filled cartridges.

SUMMARY

It is an object of the present disclosure to provide an improved cap assembly of a drug delivery device and, hence, an improved drug delivery device. This object may be achieved by the subject matter of the independent claims. Further features are the subject matter of the dependent claims.

According to one aspect, a cap assembly for a drug delivery device is provided. The cap assembly may comprise a cap. The cap may be configured for covering a distal or dispensing end of the drug delivery device when attached to the device. The cap may be a multicomponent part of the cap assembly/of the drug delivery device.

The cap assembly may comprise a clip element or fixing element. The clip element may be configured to be attached to the cap. The clip element may be a multicomponent part of the cap assembly/of the drug delivery device. The clip element may comprise two components. In particular, the clip element may comprise a first component and a second component. The first and the second component may be integrally formed, respectively. In other words, each one of the first and the second component may be a single-piece component.

The first component may be at least partly received by the second component. The second component may be adapted and arranged to hide the first component, thereby protecting the first component from scratches and further environmental influences. The second component may constitute an outer shell of the clip element. The first component and the second component may be firmly connected to one another. In particular, movement of the first component with respect to the second component and vice versa may be prevented once connected to one another. Preferably, the first component and the second component may be non-releasably connected to one another.

The second component may be attached to the cap by the connection between the first component and the second component. In other words, there is only an indirect connection between the second component and the cap. In particular, the second component may be connected to the cap via the first component. The first component may, thus, have the function of an intermediate component for connecting the second component to the cap. Further means for connecting the second component to the cap may be redundant.

The connection between the first component and the second component may be the means by which the second component is attached to the cap.

The second component may provide a high quality and hard wearing exterior surface of the clip element. Thus, provision of a robust and long-living device is facilitated. The second component may further provide a very aesthetically pleasing surface of the clip element. The first component may provide the functionality of the clip element, i.e. it may enable to attach the clip element to a further component, e.g. a jacket pocket of a user. Hence, provision of an effective and user-friendly device is facilitated.

According to an embodiment, the second component comprises a retaining feature. The second component may comprise at least one retaining feature, e.g. two or more retaining features. The retaining feature may extend along the second component. The retaining feature may be configured to retain the first component in a predefined position with respect to the second component and vice versa.

The retaining feature may comprise folded over side walls of the second component. The fold over may be greater than 90 degrees with respect to a lateral axis of the clip element, e.g. 91 or 95 degrees. The fold over may be less than 100 degrees. The first component may be at least partly received between the folded over side walls.

The second component may be adapted to be elastically deformed when the first component is placed between the folded over side wall. The first component and/or the second component may be held in place by means of the folded over side walls. As the fold over of the side walls is just greater than 90 degrees, the second component and the first component may be reliably connected to one another.

The folded over side walls may provide rigidity along a length of the second component and, hence, of the clip element. Hence, a very robust clip element is provided. Moreover, the folded over side walls may hide the first component in a manner that visually gives the impression that the clip element consists only of the second component. Once the first and the second component are connected to one another, the folded edges of the side walls may no longer be visible. The side walls may provide for clean lines and a smooth outer surface of the clip element. Accordingly, provision of a very aesthetically pleasing clip element is achieved.

According to an embodiment, the first component is at least partly or locally flexible and/or elastically deformable. In particular, the first component may comprise a flexible tip. The tip may constitute a thinned end section, in particular a proximal end section, of the first component. In particular, a thickness of the tip may be less than a thickness of further sections of the first component. In other words, the tip may comprise a smaller radial extension as compared to the further sections of the first component.

The tip may be adapted and arranged to be radially flexible. The second component may provide a cavity or clearance region. The cavity preferably receives or interacts with the flexible tip. The tip may flex into the cavity of the second component. In this way, a measure of retention is provided by the clip element, when the device is placed into a jacket pocket. Hence, provision of a reliable and user-friendly device is facilitated.

According to an embodiment, the first component comprises a first material and the second component comprises a second material. The first material and the second material may be different from one another. Overall, the second material may be more rigid or stiff than the first material. In particular, the material that the second component is made of may be intrinsically around 70 times stiffer than the material of the first component. Once assembled, the second component may provide most of the rigidity of the clip element in use. During assembly, the large majority of the elastic deformation comes from the second component rather than from the first component due to their geometry. The second component may form a C-section when viewed in cross section. This allows a relatively large amount of flexibility of the tips of the 'C'. The first component may act as a solid block in compression and is, therefore, less flexible.

According to an embodiment, the second component is press fitted to the first component. The second component may be clipped onto the first component. When the second component is clipped onto the first component, the second component may be elastically deformed. When the first and second component have reached an end position with respect to each other, the second component may spring back for retention. In this way, a cap assembly is provided which may be easily and, hence, cost-effective assembled.

According to an embodiment, the first component comprises plastic. The first component may be made of POM plastic, for example. Thereby, the first component may be manufactured cost-efficiently, e.g. by injection moulding. This facilitates provision of a light-weight and cost-effective clip element.

According to an embodiment, the second component comprises metal. The second component may be stamped from a metal sheet and, afterwards, plated to provide the desired surface hardness and finish. The second component may be made of steel, for example. Accordingly, the second component may be made very tough or hard-wearing. Moreover, also in terms of design, a metallic second component may be advantageous and/or desirable.

According to an embodiment, the second component comprises fibreglass. In this way, a very robust and hard-wearing second component may be achieved.

According to an embodiment, the clip element, in particular its first component, comprises a connection feature. The cap assembly, in particular the cap, may further comprise an outer part with an opening, and an inner part being located inside of the outer part. The inner part may further comprise a corresponding connection feature. A section of the first component may extend through the opening of the outer part such that the first component is, preferably reliably, connected to the inner part by an interaction of the connection feature and the corresponding connection feature. The interaction of the connection feature and the corresponding connection feature may be a snap interaction. This allows for a cost-effective and easy connection of the clip element, in particular the first component, and the inner part.

According to an embodiment, the clip element is configured such that the connection feature blocks movement of the inner part with respect to the outer part such that the inner part is retained within the outer part. Particularly, a proximal movement of the inner part with respect to the outer part may be blocked by the connection feature. Expediently, this allows for securing of the inner part with respect to the outer part. The clip element, the cap and the cap assembly may comprise a longitudinal axis. The longitudinal axis may extend through a proximal end of the clip element/cap/cap assembly and a distal end of the clip element/cap/cap assembly.

The "distal end" of the clip element, the cap, the cap assembly, the drug delivery device or a component of the clip element, the cap, the assembly and/or the device may mean the end which is closest to a dispensing end of the drug delivery device. The "proximal end" of the clip element, the cap, the cap assembly, the drug delivery device or a component of the clip element, the cap, the assembly and/or the device may mean the end which is furthest away from the dispensing end of the device.

According to an embodiment, the clip element is configured to block movement of the outer part with respect to the inner part. Particularly, distal movement of the outer part with respect to the inner part may be blocked by the fixing element. Advantageously, the outer part may, thereby, be secured with respect to the inner part.

According to an embodiment, the first component of the clip element comprises a guiding element comprising a T-shaped section. The outer part and/or the inner part may comprise a corresponding guiding feature. By means of the T-shaped section, measures may be provided which, particularly, prevent a radial movement of the clip element with respect to the outer part.

According to an embodiment, the first component of the clip element comprises an attachment feature. The outer part may comprises a depression which is axially spaced from the opening. The attachment feature may be in contact with or in close proximity to the depression on the outer part. The attachment feature may extend into the depression, for example. According to this embodiment, a fixation or attachment of the cap assembly or the drug delivery device to the further element, e.g. a jacket pocket, may be facilitated. Particularly, the contact, preferably a mechanical contact, of the attachment feature and the depression may increase the friction between the attachment feature and the outer part and, therewith, the reliability of the attachment or fixation of the cap assembly and the further element. In other words, the cap assembly and/or the drug delivery device may be secured or attached to the further element more securely.

According to an embodiment, the clip element is configured as a pocket clip or fixing clip. The clip element may be designed to fix the cap assembly to a pocket of an article of clothing, for example a pocket in a shirt, a jacket, or trousers, or within a carry-on item, e.g. in a pocket of the carry-on item. The carry-on item may be a bag, a backpack, a suitcase, or a trolley case, for example.

A further aspect relates to a drug delivery device. The device may comprise a cap assembly. In particular, the device may comprise the cap assembly described above. The device may be a reusable drug delivery device. In other words, the device may comprise an exchangeable cartridge.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A further aspect relates to a method for assembling a clip element for a cap assembly. The cap assembly and the clip element may correspond to the previously described cap assembly and clip element. All features described in connection with the cap assembly and the clip element apply also for the method and vice versa.

In a first method step, a first component of the clip element may be provided. The first component may be injection moulded, for example. The first component may be a plastic component. In a second step, a second component of the clip element may be provided. The second component may be stamped off a metal sheet for example. The second component may be a metal component. In cross-section, the second component may be shaped C-like.

In a next step, the second component may be clipped onto the first component. The first component and the second component may be press-fitted to one another. The second component may elastically deform when the second component is clipped onto the first component. In this way, a firm connection may be established between the first and the second component. Furthermore, a robust and long-living clip element having a very aesthetically pleasing surface may be provided in this way.

A further aspect relates to a method for assembling a cap assembly. The cap assembly may correspond to the previously described cap assembly. All features described in connection with the cap assembly also apply for the method of assembling the cap assembly and vice versa.

In a first step, a cap may be provided. Further, a first component and a second component of a clip element may be provided. The clip element and the cap may correspond to the previously described clip element and cap. In a next step, the first component of the clip element may be connected to the cap. The first component may be connected directly to the cap. The first component may be connected to the cap due to mechanical interaction with the cap, in particular with an inner part of the cap. The first component may be connected to the cap before connecting the first and the second component to one another for forming the clip element.

In a further step, the clip element may be assembled. The clip element may be assembled as set forth above. In particular, the second component may be clipped onto the first component. The second component may be indirectly connected to the cap via the first component, in particular via the connection between the first and the second component. Connection means for connecting the second component to the cap may be redundant. In this way, a robust and cost-effective cap assembly may be provided which can be easily assembled.

BRIEF DESCRIPTION OF THE FIGURES

Features which are described herein above and below in conjunction with different aspects or embodiments, may also apply for other aspects and embodiments. Further features and advantageous embodiments of the subject-matter of the disclosure will become apparent from the following description of the exemplary embodiment in conjunction with the figures, in which:

FIG. 1 shows a drug delivery device with a cap attached in accordance with one or more embodiments of the present disclosure;

FIG. 2 shows the drug delivery device of FIG. 1 with the cap removed and a dose of 79 units dialed;

FIG. 35 shows a perspective view of a clip element;

FIG. 36 shows a perspective view of the cap assembly of FIG. 32;

FIG. 37 shows a sectional view of the cap assembly of FIG. 32;

FIG. 38 shows a perspective view of a clip element;

FIG. 39 shows a perspective view of details of the clip element of FIG. 38.

DETAILED DESCRIPTION

Figure 3:
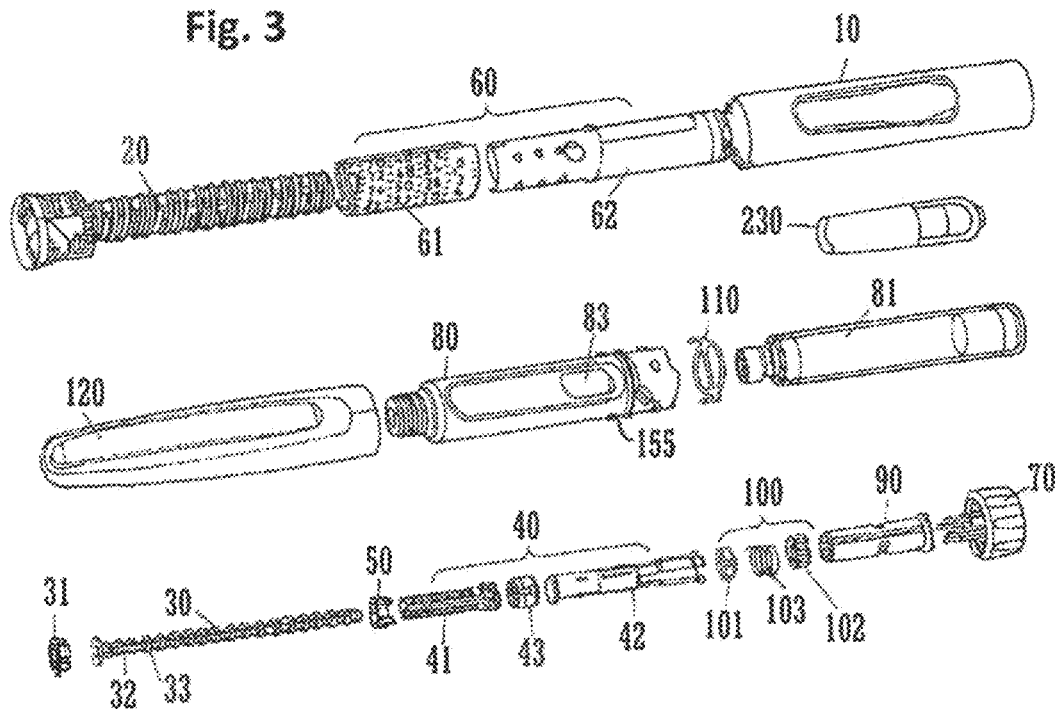
FIG. 3 shows in an exploded view the components of the drug delivery device of FIG. 1.

Like elements, elements of the same kind and identically acting elements may be provided with the same reference numerals in the figures. Additionally, the figures may be not true to scale. Rather, certain features may be depicted in an exaggerated fashion for better illustration of important principles.

FIGS. 1 and 2 show a drug delivery device 1 in the form of an injection pen. The device 1 has a distal end (lower end in FIG. 1) and a proximal end (upper end in FIG. 1). The components of the drug delivery device 1 are shown in FIG. 3 in more detail. The drug delivery device 1 comprises an outer housing part 10, an inner body 20, a piston rod 30, a driver 40, a nut 50, a display member 60, a button 70, a cartridge holder 80 for receiving a cartridge 81, a clutch 90, a clicker 100, a spring 110, a cap 120 and a window insert 230. A needle arrangement (not shown) comprising a needle hub and a needle cover may be provided as additional components, which can be exchanged. The piston rod 30 comprises a bearing 31. The driver 40 comprises a distal driver part 41, a proximal driver part 42 and a coupler 43.

The display member 60 comprises a number sleeve 61 and a dial sleeve 62. The clicker 100 comprises a distal clicker part 101, a proximal clicker part 102 and a spring 103.

Figure 4:
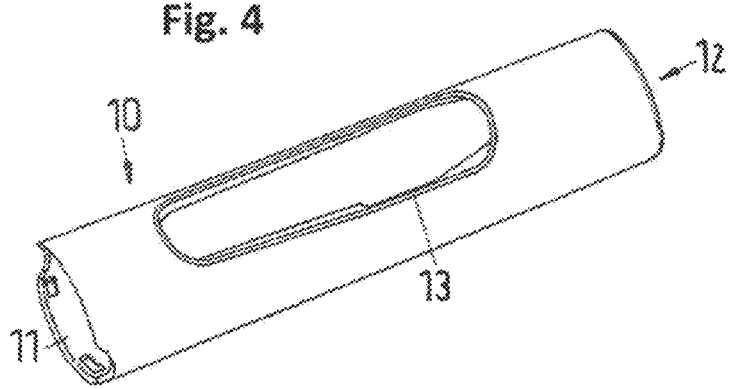
FIG. 4 shows the outer body of the drug delivery device of FIG. 1.

The outer housing part 10, which is shown in FIG. 4, is a generally tubular element having a distal part 11 for attaching the inner body 20 and a proximal part, which is provided with a rotational hard stop 12 on its inner surface (not shown) which contact mating faces of the display member 60 when the maximum units (in this example 80U) stop is engaged. The end face also serves as the end of dose dispense stop for the button 70, and the bore in the end face centers the display member 60 during both dialing and dispense. An aperture 13 is provided for receiving window insert 230. The outer body 10 provides the user with a surface to grip and react against during dispense.

Figure 17:
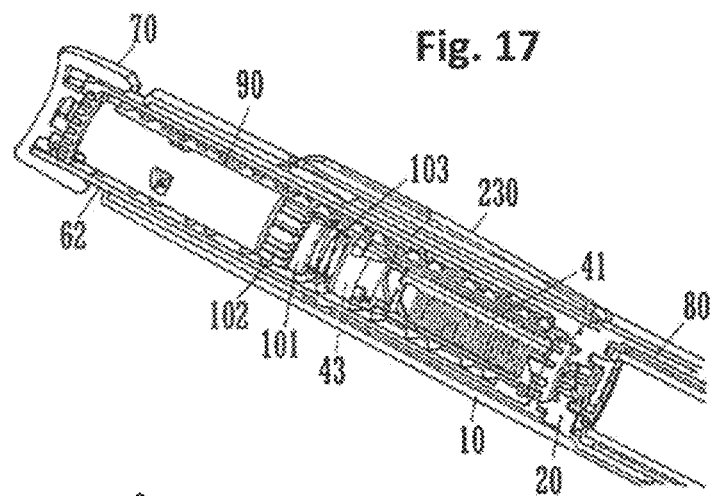
FIG. 17 shows a cut-away view of the proximal part of the drug delivery device of FIG. 1 in a zero unit position with the button released.
Figure 18:
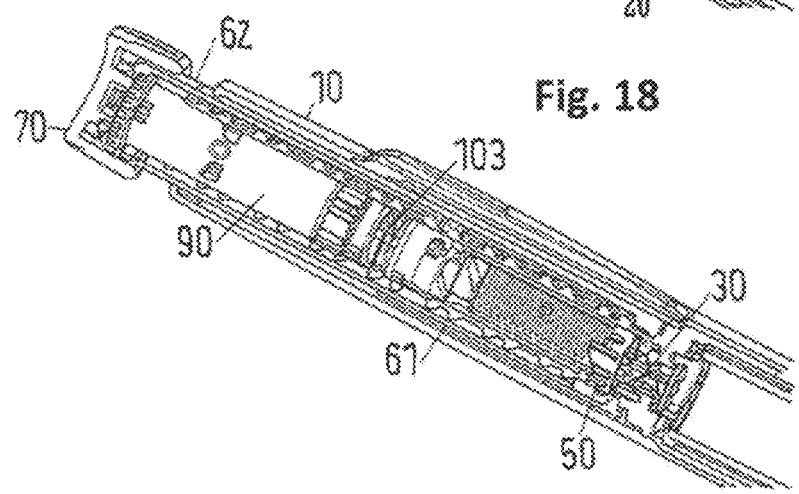
FIG. 18 shows a cut-away view of the proximal part of the drug delivery device of FIG. 1 in a position with some units dialed.
Figure 19:
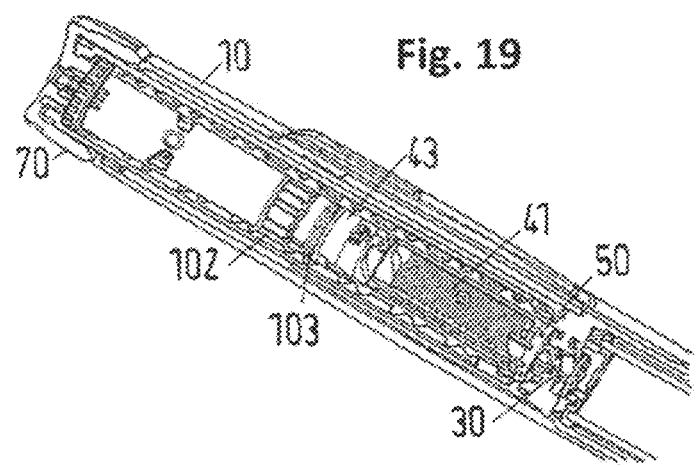
FIG. 19 shows a cut-away view of the proximal part of the drug delivery device of FIG. 1 in a zero unit position with the button pressed.

The inner body 20 is a generally tubular element having different diameter regions. As can be seen in FIGS. 17 to 19, the inner body 20 is received in the outer body 10 and permanently fixed therein to prevent any relative movement of the inner body 20 with respect to the outer body 10. The inner body has the functions to house the drive mechanism within, guiding the clickers and the last dose nut 50 via internal splines, to provide an internal thread through which the piston rod 30 (lead screw) is driven, to support and guide the number sleeve 61 and the dial sleeve 62 on an external thread form, to secure the cartridge holder 80 and to secure the outer body 10 and the window insert 230.

The outermost diameter of the inner body 20 also forms part of the visual design and remains visible when the cap 120 is secured to the cartridge holder 80 as a ring separating the cap 120 from the outer body 10. This visible ring also has depressions which align with the cap snap features on the cartridge holder 80 to indicate that the cartridge holder has been correctly fitted.

Figure 5A:
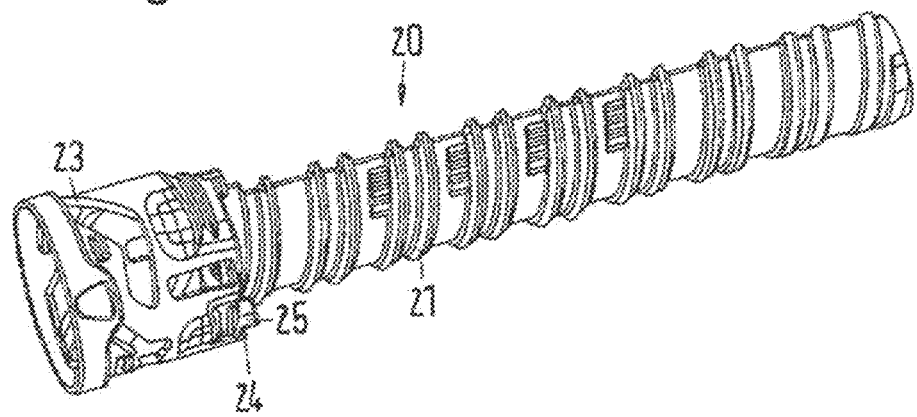
FIG. 5*a* shows the inner body of the drug delivery device of FIG. 1.
Figure 5B:
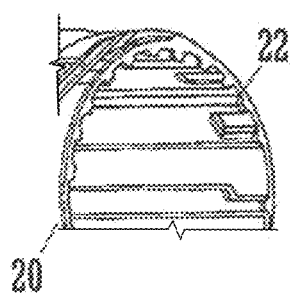

An external thread 21 is provided on the outer surface of the inner body 20. Further, splines 22 (FIG. 5b) are provided on the inner surface of the inner body 20. These internal splines 22 guide the clicker 100 axially during both dialing and dispense and also prevent the last dose nut 50 from rotating. Some of the splines may be wider to ensure correct rotational assembly of the internal components, and these wider splines may have a stepped entry and angled surface to encourage the last dose nut 50 to rotate up against the stop face on the distal drive sleeve 41 during assembly. At the open end shown in FIG. 5b there are an additional short splines which together with the alternating long splines 22 are used to rotationally lock the button 70 (dose dial grip) at the end of dispense and serve to increase the strength of the 0U dial stop when the button 70 is depressed. This is achieved by engagement with male spline features on the clutch component 90.

Bayonet features 23 guide the cartridge holder 80 into the mechanism during cartridge replacement, compressing the cartridge bias spring 110, and then back off the cartridge holder 80 a small distance in order to reduce axial play in the mechanism. Snap features inside the inner body 20 lock the cartridge holder 80 rotationally when it has been correctly fitted. The profile of these snaps aims to prevent the user from partially fitting the cartridge holder 80, the cartridge bias spring 110 ejecting the cartridge holder 80 if the snaps have not at least started to engage. A window retention nose 24 retains the window insert 230 when the outer body 10 and window insert 230 assembly is axially inserted onto the inner body 20. Two diametrically opposite stop faces 25 define the rotational end position for the number sleeve 61. This end position is the end of dose detent position for the minimum dose (0U).

The piston rod 30 is an elongate element having two external threads 32, 33 with opposite hand which overlap each other. One of these threads 32 engages the inner thread of the inner body 20. A disk-like bearing 31 is provided at the distal end of the piston rod 30. The bearing 31 may be a separate component as shown in FIG. 3 or may be attached to the piston rod 30 as a one-piece component via a predetermined breaking point.

The piston rod 30 transfers the dispense load from the driver 40 to the bearing 31, creating a mechanical advantage greater than 1:1 by converting the torque generated on the piston rod 30 by the driver 40 thread interface into additional axial load as the piston rod passes through the thread in the inner body 20. The piston rod 30 is reset by pressing on the bearing 31 and this in turn rotates the piston rod back into the inner body 20. This disengages and then rotates the distal drive sleeve 41, resetting the last dose nut 50 back to its starting position on the distal drive sleeve 41.

Figure 9:
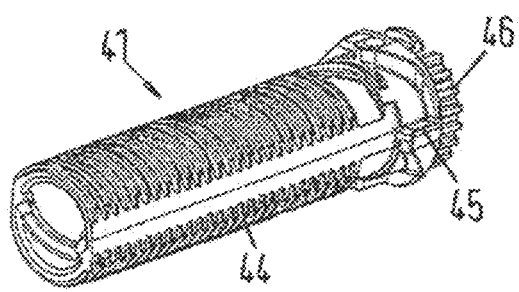
FIG. 9 shows a first driver component of the drug delivery device of FIG. 1.
Figure 10:
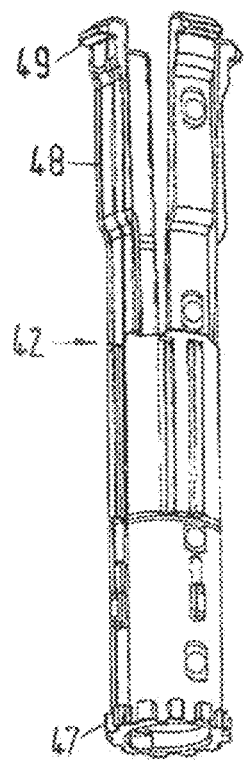
FIG. 10 shows a second driver component of the drug delivery device of FIG. 1.
Figure 11:
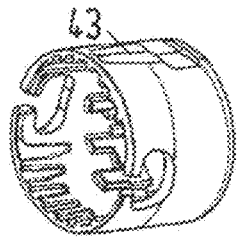
FIG. 11 shows a third driver component of the drug delivery device of FIG. 1.
Figure 12:
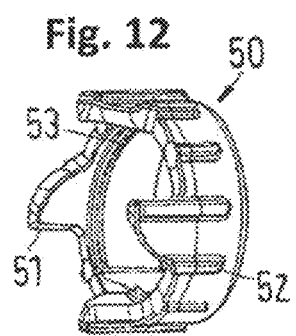
FIG. 12 shows the last dose nut of the drug delivery device of FIG. 1.
Figure 13:
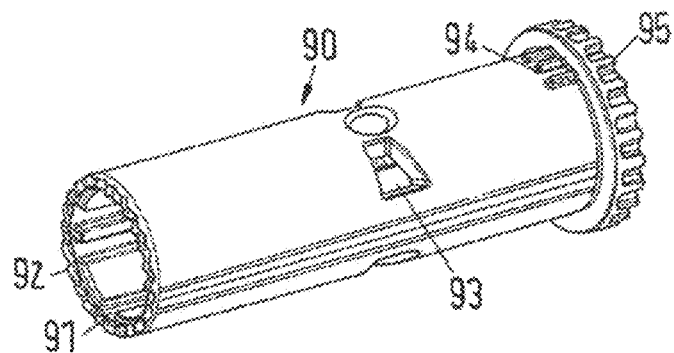
FIG. 13 shows a clutch component of the drug delivery device of FIG. 1.
Figure 14:
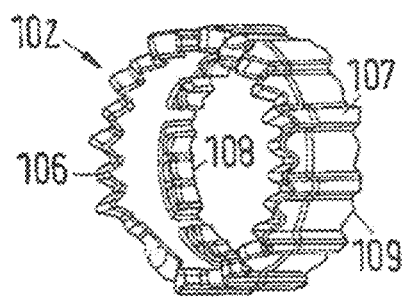
FIG. 14 shows a first clicker component of the drug delivery device of FIG. 1.
Figure 15:
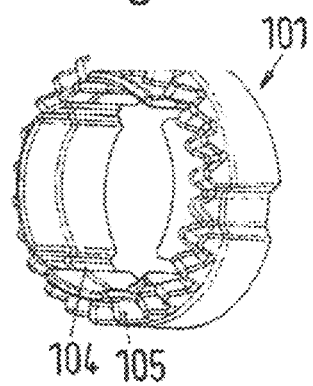
FIG. 15 shows a second clicker component of the drug delivery device of FIG. 1.

The driver 40 is a generally tubular element having in the embodiment shown in the Figures three components which are depicted in FIGS. 9 to 11 in more detail.

The distal drive sleeve 41 engages with the piston rod thread 33 to drive the piston rod 30 through the inner body 20 during dose delivery. The distal drive sleeve 41 is also permanently connected to the coupler 43 which in turn is releasably engaged through reset clutch features to the proximal drive sleeve 42. The two halves of the drive sleeve are rotationally and axially connected during dialing and dispense, but are de-coupled rotationally during device reset so that they can rotate relative to each other.

The external thread 44 engages with the last dose nut 50. The thread form has three stages, a shallow first stage (left hand side in FIG. 9) over which the nut 50 travels to count the majority of the units dialed, a fast stage over which the last dose nut moves rapidly axially prior to engaging the stop faces, and a final shallow section which ensures that when the stop faces have engaged, the axial restraint on the nut 50 extends over a reasonable length of thread form. Four equi-spaced stop faces 45 engage with mating stop faces 51 on the last dose nut 50 to limit the number of units that can be dialed. Splines 46 are provided at the proximal end of distal drive sleeve 41 to transfer torque from or to the coupler 43, which may be snapped on the distal drive sleeve 41.

The proximal drive sleeve 42 shown in FIG. 10 supports the clicker components 100 and the clutch 90 and transfers rotational movement from the dose button 90 to the coupler 42 and distal drive sleeve 41.

Teeth features 47 located at the distal end of proximal drive sleeve 42 engage with the reset clutch features on the coupler 43 to connect both halves of the drive sleeve during dialing and dispense. During reset these teeth 47 disengage.

Several splines are provided on the outer surface of proximal drive sleeve 42 engaging with the distal and/or proximal clicker part 101,102, preventing relative rotation during dialing and dispense. Further splines, which are located in the middle region of proximal drive sleeve 42, engage with the clutch 90 component. They may be arranged to be non-rotationally symmetric so that the various clicker components cannot be assembled accidentally upside down.

The proximal portion of proximal drive sleeve 42 has four arms or fingers 48. A hook-like bearing surface 49 exists on the underside (as seen in FIG. 10) of flange segments on the end of the flexible fingers 48. The flexible fingers 48 are separated with gaps or slots that make space for the button 70 to snap to the clutch 90 and also enable these fingers to flex inwards during assembly of the proximal drive sleeve 42 to the dial sleeve 62. After assembly the hooks 49 retain the proximal drive sleeve 42 relative to the dial sleeve 62 under the reaction force from the spring 103. During dispense the button 70 depresses the spring 103 via the clutch 90 and the clicker components and this spring 103 is reacted through the coupler 43 to the proximal drive sleeve 42 which then through these bearing surfaces applies axial load to the dial sleeve 62. This axial load drives the dial sleeve 62 and hence number sleeve 61 along the helical thread of the inner body 20, back into the body of the device, until the 0U stop faces on the number sleeve 61 contact the inner body 20.

The coupler 43 shown in FIG. 11 rotationally couples the two halves of the drive sleeve together during dialing and dispense, whilst allowing them to de-couple during reset. The coupler 43 has to also transfer the last dose protection stop load from the proximal drive sleeve 42 to the distal drive sleeve 41. Two sets of teeth are provided in the coupler 43 for engaging teeth 46 and teeth 47, respectively. The coupler 43 is snapped onto distal drive sleeve 41 allowing limited relative axial movement with respect to the proximal drive sleeve 42.

The nut 50 is provided between the inner body 20 and the distal drive sleeve 41 of driver 40. Stop faces 51 are located on the proximal face of last dose nut 50 to limit the number of units that can be dialed if the stop faces 51 contact stops 45 of distal drive sleeve 41. The function of the last dose nut 50 is to prevent the user from dialing beyond a finite amount. This limit is based on the dispensable volume of the cartridge 81 and when reached, the user must replace the cartridge 81 and reset the device.

External ribs 52 of the nut 50 engage splines 22 of inner body 20. An internal thread 53 of the nut engages the external thread 44 of distal drive sleeve 41. As an alternative, splines and ribs could be provided on the interface between the nut 50 and the driver 40 and threads could be provided on the interface between the nut 50 and the inner body 20. As a further alternative, the nut 50 may be designed as e.g. a half nut.

The display member 60 is a generally tubular element which is composed of number sleeve 61 and dial sleeve 62 which are snapped together during assembly to axially and rotationally constrain these two components, which thus act as a single part.

Figure 8:
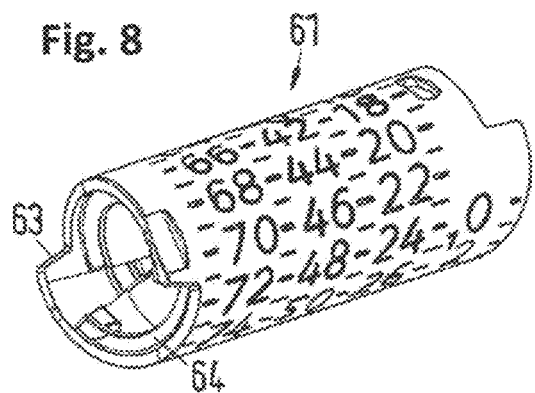
FIG. 8 shows a second display member component of the drug delivery device of FIG. 1.

The main functions of the number sleeve 61 depicted in FIG. 8 are to provide a surface onto which dose numbers can be printed to display the dialed dose, to guide the helical path of the internal mechanism during dialing to follow the helical thread form on the piston rod 30 when threaded to the inner body 20 and to attach to the dial sleeve 62.

The number sleeve 61 is designed to be fully enclosed in the outer body 10 during dialing and dispense and therefore only the dialed dose is visible to the user through the window aperture. The number sleeve has a 0U (minimum dose) stop face 63 to limit its travel when dialed in but the 80U (maximum dose) stop faces that limit the dialed out condition are located on the dial sleeve 62. At the end of each dispense stroke, this stop face 63 engages with mating surface 25 on the inner body 20 to limit the rotational position of the number sleeve 61.

A helical drive face 64 forms a thread that guides the number sleeve 61 during dialing and dispense to follow the helical path 21 on the inner body.

The dial sleeve 62 is assembled to the number sleeve 61 such that once assembled, no relative movement is allowed. The parts are made as separate components to enable both molding and assembly. Also, whereas the number sleeve 61 is preferably white to give contrast for the e.g. black dose numbers, the dial sleeve 62 color can be chosen to suit the aesthetics or perhaps to distinguish the drug type.

At the dose proximal end, the dial sleeve 62 has internal clutch features 65 that engage with the clutch component 90 during dialing and disengage from the clutch during dispense. These clutch features 65 rotationally lock the dial sleeve 62 to the clutch 90 during dialing and when the 0U and 80U stops are engaged. When the button 70 is depressed these clutch features disengage to allow the clutch 90 and drive mechanism to move axially whilst the dial sleeve 62 and number sleeve 61 spin back to the 0U start position.

The dial sleeve 62 rotates out during dialing through its engagement with the clutch 90 and number sleeve 61, and rotates back in during dispense under the axial force applied by the proximal drive sleeve 42 to a flange-like bearing face 66 on the end of the dial sleeve. This bearing face 66 engages with the flexible arms 48 of the proximal drive sleeve 42 during dispense. Two diametrically opposite faces 67 engage with the outer body 10 when the maximum dose (e.g. 80U) has been dialed, forming the maximum dose stop faces.

A ratchet arm 68 engages with ratchet features on the button 70 (dose dial grip) to provide audible feedback during dispense, giving one click per unit delivered. Further, this prevents the user from gripping and rotating the number sleeve 61 outwards from a partially dialed out position whilst holding the button 70 pressed in. This would back wind the piston rod 30 which would result in an under dose on the subsequent dialed dose. It may further strengthen the 0U stop.

Figure 16:
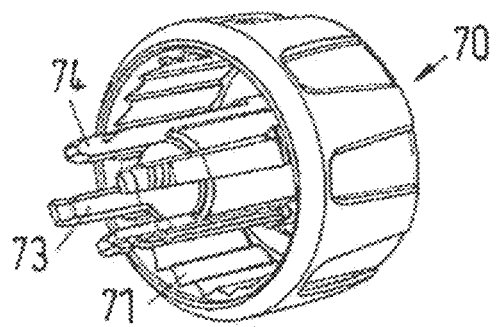
FIG. 16 shows the button of the drug delivery device of FIG. 1.

The button 70 which is shown in FIG. 16 serves as a dose dial grip and is retained by the clutch 90 to transfer the actions of the user to the clutch. It also carries ratchet teeth 71 that engage the ratchet arm 68 on the dial sleeve 62, which serves as the dispensing clicker giving audible feedback (ratchet clicks), and an end face 72 which serves as the dose completion stop face with the outer body 10. This end face 72 thus serves to define the end position during dispense when it contacts the outer body 10 to provide a very positive stop improving dose accuracy.

A central sleeve-like portion of button 70 is provided with four arms 73 having hook-like snap features 74 at their respective distal ends. The arms 73 form splined surfaces engaging with the clutch 90 to transfer torque from the button 70 through the clutch to the dial sleeve 62 and proximal drive sleeve 42. The snap features 74 engage apertures in the clutch 90 and are designed with angled undercut faces to maintain engagement when an axial load is applied to pull the button 70 out of the pen body 10. The space between arms 73 defines pockets giving clearance for the flexible arms 48 of proximal drive sleeve 42 to slide freely relative to the button 70 and clutch 90 when the button 70 is depressed and released during dose dispense.

Figure 6:
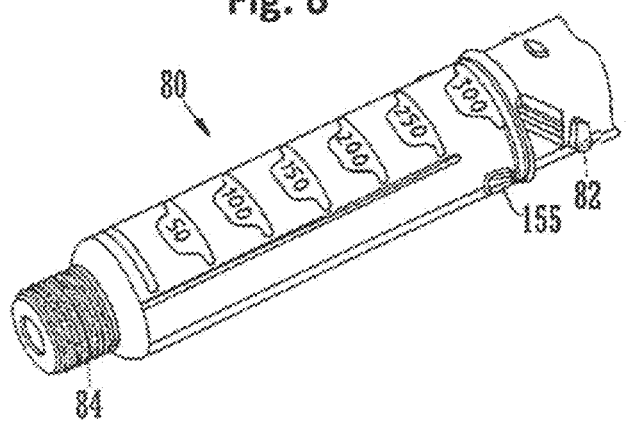
FIG. 6 shows the cartridge holder of the drug delivery device of FIG. 1.
Figure 7A:
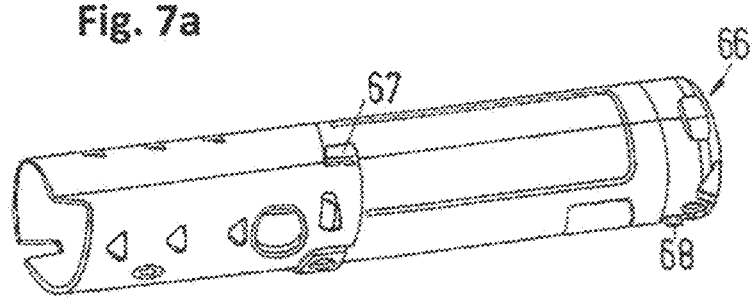
FIG. 7*a* shows a first display member component of the drug delivery device of FIG. 1.
Figure 7B:
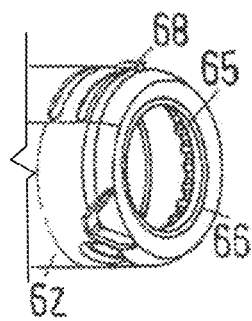
FIG. 7*b* shows a detail of the first display member of FIG. 7*a*.

The cartridge holder 80 attaches to the inner body 20 with a bayonet connection 82 and houses the glass ampoule or cartridge 81 containing the medication to be dispensed. The cartridge holder 80 includes an aperture 83 in the rear face (as seen in FIG. 6) which if gripped by the user prevents the ampoule from falling out when the cartridge holder is removed from the inner body 20. The front face is printed with a dose number scale. The threaded distal end 84 is used to attach disposable pen needles.

A tubular clutch 90 is provided between the display member 60 and the button 70. The clutch is fixed relative to and retains the button 70 and together they travel axially relative to the proximal drive sleeve 42 when the button 70 is depressed during dispense, disengaging the clutch teeth from the dial sleeve 62. It also transfers torque from the button to the proximal drive sleeve 42, and the dialing and 0U/80U stop loads from the button via the clutch teeth to the dial sleeve and number sleeve.

Drive sleeve splines 91 provided on an inner surface of the clutch engage with the proximal drive sleeve 42. At the distal end face, clutch biasing teeth 92 are provided which mate with similar teeth on the proximal clicker part 102 to ensure that in the button out position (dialed dose) the clutch is locked in rotation to the proximal clicker part 102 under the biasing action of the clutch spring 103. The teeth 92 are shallow in height to prevent the proximal clicker part 102 from engaging with splines on the proximal drive sleeve 42 during dialing. Four snap apertures 93 serve to retain the snap features 74 of button 70. Near its proximal end, the clutch has splines 94 which at the end of dispense with the button 70 depressed lock to the inner body 20 to prevent the user from rotating the button 70 below the 0U position.

Clutch teeth 95 engage with clutch teeth 65 of the dial sleeve to rotationally couple the button 70 via the clutch to the number sleeve 61. During dispense the clutch is moved axially so as to disengage these clutch teeth 95 releasing the dial sleeve 62 to rotate back into the device whilst the clutch 90 and hence driver 40 move axially to dispense the dose.

The clicker 100 comprises a distal clicker part 101, a proximal clicker part 102 and a spring 103. The clutch spring 103 serves to bias the button 70 out so that at the end of a dose the button 70 pops out, re-engaging the clutch 90 with the dial sleeve 62 ready for dialing. Further, it provides the spring force for the clicker components to act as clickers and also as detent positions for the number sleeve 61. In addition, it holds the two halves of the drive sleeves 41, 42 in rotational engagement during dialing and dispense, whilst allowing them to disengage during device reset.

The distal clicker part 101 is permanently splined to the proximal drive sleeve 42 and engages with the proximal clicker part 102 which in turn is splined to the inner body 20. During dialing when the drive sleeve is rotated relative to the inner body, the two clickers 101, 102, rotate relative to each other under the compression force of the clutch spring 103. This force combined with the clicker teeth formed on the end face of each clicker provides the clicks and also the detent dialing positions.

During dispense the two clickers 101, 102 are pressed together under the dispense load and therefore prevent relative rotation between the proximal drive sleeve 42 and inner body 20, driving the piston rod forwards to deliver the dose. The splines 104 on the inner bore rotationally couple the distal clicker part 101 to the proximal drive sleeve 42 at all times, but allow free axial movement when the button 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body during both dialing and dispense, providing clicks during dialing and locking the proximal drive sleeve 42 in rotation during dispense. Additional cylindrically shaped splines 108 also couple the proximal clicker part 102 rotationally to the proximal drive sleeve 42 when the button 70 is depressed, this preventing the user from dialing past 80 units with the button depressed. Proximal clicker part 102, in addition to the primary clicker teeth 106, has clutch biasing teeth 109 on the opposite end face. These teeth mate with similar teeth 92 on the clutch to ensure that in the button out position (dialed dose) the clutch is locked in rotation to the proximal clicker part 102 under the biasing action of clutch spring 103.

The cartridge bias spring 110 is assembled as two components one after the other, the lower first and the upper second. The spring combination serves to apply an end load to the cartridge 81 at extremes of tolerance so as to bias it forwards onto the end face of the ferrule in the cartridge holder 80. This ensures that when the user removes and attaches a needle, the friction between the needle cannula and septum of the cartridge does not move the cartridge 81 axially relative to the cartridge holder 80. The bias spring 110 also acts to provide a force against which the user has to connect the cartridge holder 80 and this may add to the tactile feedback of this bayonet joint. The spring 100 also serves to eject the cartridge holder 80 if the cartridge holder is not rotated into a secure position, highlighting this error to the user.

The cap 120 serves to protect the cartridge holder 80 from damage and the cartridge 81 itself from dust dirt ingress on to the area around the septum. The cap 120 is designed to accommodate a standard pen injector needle. The cap 120 comprises a clip element 134 or fixing element for attaching the cap 120 and, hence, the drug delivery device 1 to a further element, e.g. a jacket pocket of the user. Preferably, the clip element 134 is snap-fitted to the cap 120. Details concerning the structure of the cap 120 and the clip element 134 as well as their connection are described later on.

The window insert 230 may include a lens to magnify the dose numbers e.g. by approximately 25% from their printed size. The window insert 230 may be back printed to protect the printed surface from abrasion and also to maximize the light entering through the window aperture, giving uniform illumination of the dose numbers and white area around these numbers. Arrows may be printed adjacent to the window aperture that indicate the dose dialed.

In the following, the function of the drug delivery device and its components will be explained in more detail with reference to FIGS. 17 to 19.

To use the device, a user has to select a dose. In the start (at rest) condition as shown in FIG. 17 the display member 60 indicates the number of doses dialed to the user. The number of dialed units can be viewed through the dose window 230 in the outer body 10. Due to the threaded engagement between the display member 60 and the inner body 20 rotation of the button 70 in a clockwise fashion causes the display member 60 to wind out of the device and incrementally count the number of units to be delivered. FIG. 18 shows an intermediate stage of dialing (e.g. 7 of 80 units).

During dose setting button 70, driver 40 and display member 60 are rotationally locked together via clutch 90. Further, button 70, driver 40 and display member 60 are axially coupled. Thus, these three components wind out of the outer housing 10 during dose setting. Clockwise rotation of the button 70 causes the driver 40 to rotate and in doing so it advances along the piston rod 30 which remains fixed throughout dialing. The clicker arrangement 100 provides tactile and audible feedback to the user when dialing doses. At the maximum settable dose of 80 units, the stop features 12 and 67 engage to prevent further dialing.

The last dose nut 50 provides the function of counting the number of dispensed units. The nut 50 locks the device at the end of cartridge life and as such no more drug can be dialed by the user. The last dose nut 50 and the driver 40 are connected via a threaded interface as explained above. Further, the last dose nut 50 is assembled into splines 22 such that the nut 50 and the inner body 20 are rotationally locked together (at all times). Rotation of the driver 40 during dialing causes the nut 50 to advance along the thread 44. The nut 50 is free to slide axially within the inner body 20 at all times which allows advancement of the nut. The change in pitch of thread 44 shown in FIG. 9 towards the final doses axially accelerates the advancement of the nut 50 towards the end of cartridge life lockout condition. At the end of life condition, the stop features 51 of the last dose nut 50 contact the corresponding features 45 on the driver 40. The splined contact with inner body 20 reacts any torque transmitted by these stop features 45.

With the desired dose dialed, the device 1 is ready for dose dispensing. This basically requires pushing button 70 which will result in a disengagement of the clutch 90 from dial sleeve 62 thus allowing relative rotation between the display member 60 and the button 70. In all conditions the driver 40 and the button 70 are rotationally locked together by engagement of arms 73 and fingers 48 and by splines 91 engaging corresponding splines on proximal drive sleeve 42. Thus, with the clutch 90 disengaged (button 70 pushed in) button 70 and driver 40 are rotationally locked together with the button 70, the driver 40 and the display member 60 still being axially coupled.

When dispensing a dose, the dose button 70 and clutch 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the mechanism is forced to move axially whilst the dial sleeve 62 and number sleeve 61 are free to spin back into the outer housing 10. The interaction of mating threads between the piston rod 30, driver 40 and inner body 20 delivers a mechanical advantage of 2:1. In other words, axially advancing driver 40 causes the piston rod 30 to rotate which due to the threaded engagement of piston rod 30 with the inner body 20 advances the piston rod. During dose dispensing dispense clicker 68, 71 is active which involves button 70 and display member 60. The dispense clicker provides primarily audible feedback to the user that drug is being dispensed.

The end of this step is shown in FIG. 19. At this point the dose is complete and when the user removes the force from the end of the dose button 70, the clutch spring 103 pushes this dose button 70 rearwards, re-engaging the teeth 65 and 95 between the clutch and the dial sleeve.

Resetting the device starts with removal of the cartridge holder 80 and replacing an empty cartridge with a full cartridge 81. As the cartridge holder is re-attached, the bung of the new cartridge contacts bearing 31, thus pushing piston rod 30 back into the housing. Initially, the piston rod 30 screws into the inner body 20, thereby axially disengaging the coupler 43 from the proximal drive sleeve 42 against the biasing force of spring 103. Once disengaged the coupler 43 is free to start rotating together with distal drive sleeve 41 and continues to do so as the cartridge holder 80 is moved axially into engagement with the inner body 20. Thus, the distal drive sleeve 41 rotates with respect to the proximal drive sleeve 42 which is still rotationally constrained in inner body 20 as clicker parts 101 and 102 are pressed together by compressed spring 103. As the distal drive sleeve 41 rotates, last dose nut 50 is reset to its (distal) start position. Coupling the cartridge holder 80 to inner body 20 backs off the mechanism due to the bayonet structure 23 allowing re-engagement of the proximal drive sleeve 42 with coupler 43 and thus the distal drive sleeve 41.

In the following the cap 120 is described in more detail with reference to FIGS. 20 to 25.

The cap 120 having a distal end 121 and a proximal end 122 serves to cover and protect the cartridge holder 80 from damage and the cartridge 81 itself from dust and dirt ingress on to the area around the septum. The cap 120 is designed to accommodate a distal part of the pen injector which is moved into the cap 120 through a proximal opening of the cap 120. The cap 120 may be attached to the drug delivery device 1 is such a manner that the needle arrangement 180 attached to the cartridge and the cartridge holder 80 are located inside the cap 120. The cap 120 is detached before use of the drug delivery device 1. The inside of the cap 120 is formed such that there is enough space for the needle arrangement 180 attached to the cartridge and the cartridge holder 80. Means (not shown) for guiding and holding the cartridge holder 80 and the needle arrangement 180 may be provided on the inner surface of the cap 120.

Figure 20:
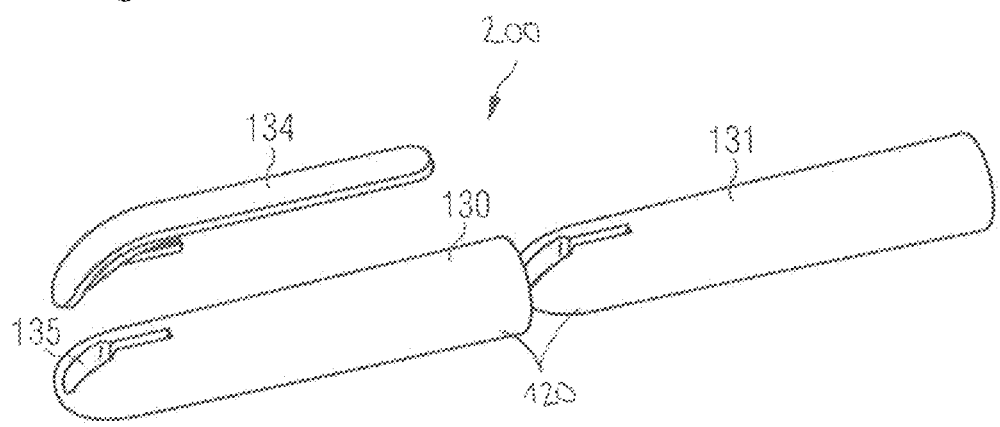
FIG. 20 shows an exploded view of a cap assembly.

FIG. 20 shows an exploded view of the cap 120 comprising an outer cap element 130 and an inner cap element 131. Furthermore, the clip element 134 is shown. Clip element 134 and cap 120 form together a cap assembly 200, which is described later on in detail. The outer and inner cap elements 130, 131 are made by a metal sleeve and a plastic sleeve, respectively, that can be assembled together to form the removable cap 120. The outer and inner cap elements 130, 131 are connected by suitable means, e.g. adhesive means, positive locking, friction locking and/or a snap interaction. The clip element 134 allows connection of the injector pen 1 by means of the cap 120 to a shirt or jacket pocket and is always handy for that reason. An aperture 135 in the outer cap element 130 enables the clip element 134 to snap to the inner cap element 131.

The outer cap element 130 is preferably made of metal; the inner cap element 131 is preferably made of plastic. The combination of the metal outer cap element 130 and the plastic inner cap element 131 provides a high-quality look and pleasant touch. The cap 120 is not too heavy and allows comfortable handling. The design of the inner component of the cap 120 allows retaining the clip element 134 and provides sufficient space to accommodate a standard needle and needle cover fitted to cartridge holder 80 inside the cap 120.

The outer cap element 130 may be a 0.4 to 0.6 mm thick aluminium element that provides a metal skin over the polymer inner cap element 131. The form of the cap 120 may be similar to that of a cap completely made of plastic. Such a cap 120 may substitute a cap completely made of plastic with no change in the tactile feel during attachment. Similar plastic features will not increase the risk of wear that may otherwise occur if attaching a plain metal sleeve to the existing plastic cartridge holder retention features.

The inner and outer cap elements 131, 130 are sleeve-shaped. The metal sleeve can be deep drawn from a metal sheet and then anodised over at least the outer surface. The anodising provides a high quality and hard wearing exterior surface to the cap 120 and enables the cap 120 to be given a variety of metallic colours. The removable cap 120 comprising the metal outer cap element 130 and the plastic inner cap element 131 can then be attached to a pen housing/mechanism which may be also made with a similar metal sleeve, to provide a reusable injection device that has a high quality visual appearance and a robust surface.

This design minimises cost and provides robust hard-wearing features. Hence the use of a combination of metal and plastic sleeve-shaped components enables the plastic sleeve to be moulded with features that attach to the plastic cartridge holder cap retention means.

Figure 21:
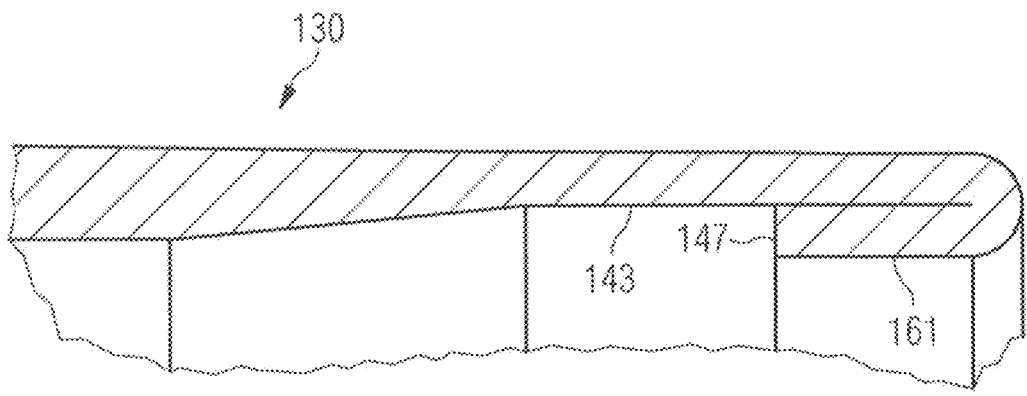
FIG. 21 shows a sectional view of a proximal region of an outer cap element.
Figure 22:
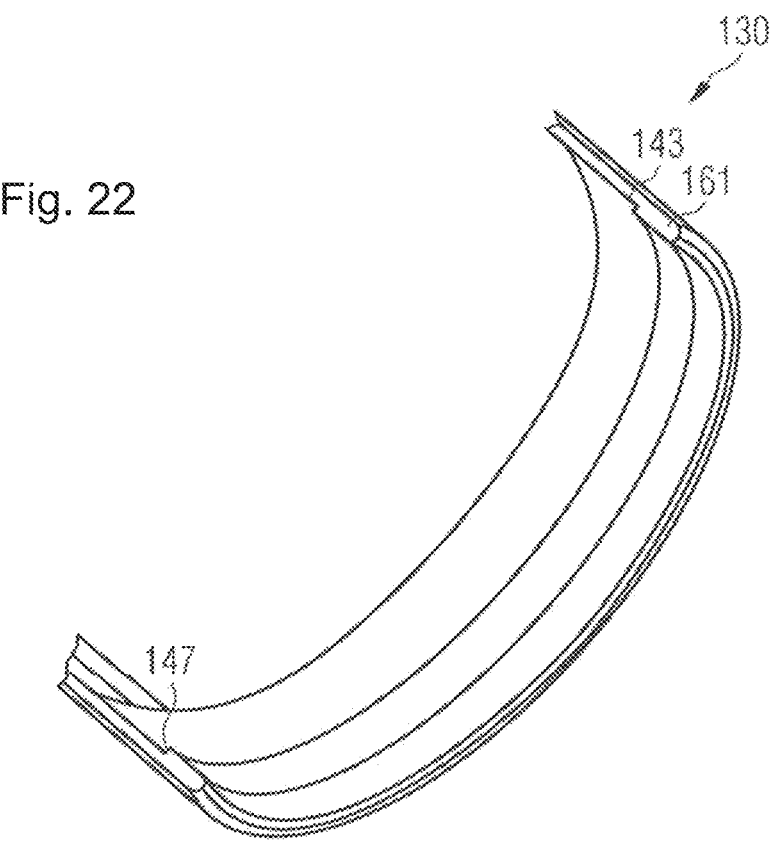
FIG. 22 shows a three-dimensional cut out view of the outer cap element.

FIG. 21 shows a sectional view of a proximal region of the outer cap element 130. FIG. 22 shows a three-dimensional cut-out view of this component. The outer cap element 130 is formed by a metal sleeve deep drawn with reduced thickness at the open end section. The very proximal region is rolled over to form a rounded or folded end 161. Such rolling back of the material may form a beading. In this embodiment the material of the outer cap element 130 has been bent once. Nevertheless, the material may be bent more than once. Such bending allows forming a sharp edge 147 on the inner surface of the outer cap element 130.

Due to the thinner material of the open end, which is created during the deep drawn process, and then forming the beading, a circumferential recess 143 is formed on the inner surface of the outer cap element 130. This recess 143 serves as space into which the inner cap element 131 can deform when attaching the cap 120 to the cartridge holder 80. The sharp edge 147 is the proximal edge of the recess 143, the edge 147 serving to retain the plastic inner cap element 131 after assembly.

Figure 23:
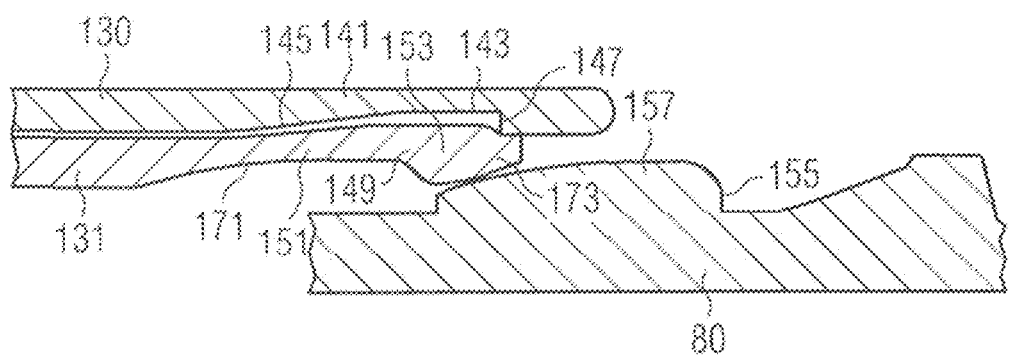
FIG. 23 shows a sectional view of the proximal section of the cap during attachment.

FIG. 23 shows a sectional view of a proximal section 141 of the cap 120 during attachment to the drug delivery device 1. During attachment the cap 120 including the inner and outer cap elements 131, 130 moves proximally with respect to the cartridge holder 80 in such a manner that the cartridge holder 80 moves into the cap 120.

The outer cap element 130 has a proximal section 141 comprising a cavity 143 on the inner surface of the outer cap element 130. The cavity 143 is formed as a circumferentially running recess in this embodiment. Alternatively the cavity 143 may have another form which may correspond with the form and size of the deformable region 151 of the inner cap element 131.

The thickness of the outer cap element 130 in the region of the cavity 143 is smaller than the thickness of a distal section or a middle section of the outer cap element 130. The distal edge 145 of the cavity 143 is formed in the shape of a ramp which allows a gentle transition between the middle section of the outer cap element 130 and the cavity 143 located in the proximal section 141. The proximal edge 147 of the cavity 143 is steeper than the distal edge 145 and may be formed as a sharp edge.

The inner cap element 131 comprises cap snap means 149 located on the inside of a proximal section of the inner cap element 131 and suitable for engaging with a cap retention means 155 located on the cartridge holder 80 of the drug delivery device 1. The cap snap means 149 is formed by at least a proximal part of the deformable region 151 that may be deformed during attachment and detachment in order to lock the cap snap means 149 to the cap retention means 155 of the drug delivery device 1 and to release the cap snap means 149 from the cap retention means 155. The cap snap feature 149 comprises a raised internal bump feature 153 or finger and a cavity 171 where the inner cap element 131 in the region of the cavity 171 is thinner than in other regions; the cavity 171 may be formed by the deformable region 151. The internal bump feature 153 has a proximal slope being less steep than a distal slope.

The reduced thickness of the inner cap element's cavity 171 enables the deformation of the cap snap means 149, thereby allowing engaging to the cap retention feature 155. Due to the cavity 143 of the outer cap element 130 there is a gap between the outer and inner cap elements 130, 131. The deformable region 151 is deformable into the cavity 143 of the outer cap element 130. In other words, the deformable region 151 is deformable into the gap between the outer and inner cap elements 130, 131.

According to one embodiment, the proximal end 173 of the cap snap means 149 extends proximally over the proximal edge 147 of the cavity 143; the proximal edge 147 preventing outwards movement of the proximal end 173 of the cap snap means 149 and to hold this end circular. According to a further embodiment, the proximal end 173 of the cap snap means 149 does not protrude over the edge 147. In particular, there may be no need for the proximal end 173 to protrude over the edge 147 as the clip holds both cap parts together axially.

The cap retention means 155 is located on the outer surface of the plastic cartridge holder 80. The cap retention means 155 comprises an elevation 157 which may have a base area formed as trapezium, circle, triangle or any other shape. In one embodiment two elevations 157 may be arranged on opposite sides of the cartridge holder 80, as shown in FIGS. 3 and 6. In one embodiment there are two or more than two elevations that are arranged equally or non-equally spaced on the drug delivery device 1.

The elevation 157 has proximal and distal slopes; the latter being less steep than the proximal slope of the elevation 157. The distal slope enables easy sliding of the proximal slope of the internal bump feature 153 over the top of the elevation 157 during attachment. The steeper slopes of both the elevation 157 and the internal bump feature 153 hinder distal movement of the internal bump feature 153 once it has moved over the top of the elevation 157, thereby preventing backward movement of the internal bump feature 153 after attachment. However, the application of a sufficient force by the user pulling the cap 120 distally pulls the internal bump feature 153 over the elevation 157 again, thereby allowing detachment of the cap 120. Since the distal slope of the internal bump feature 153 and the proximal slope of the elevation 157 are steeper, the force required for detachment is higher than for attachment, which prevents accidental detachment of the cap 120. Nevertheless, alternative internal bump feature 153 and elevation 157 embodiments may have other slope designs, which may be symmetrical.

When the internal bump feature 153 slides over the elevation 157, the internal bump feature 153 is pushed towards the outer cap element 130. Since the proximal end 173 of the cap snap means 149 is held in its position by the proximal edge 147 of the outer cap element 130, the resulting torque deforms the deformable region 151 outwardly and allows the nose tip to slide over the elevation 157. The cavity 143 of the outer cap element 130 allows space to accommodate at least some of the deformation of the plastic inner cap element 131 when the internal bump feature 153 slides over the elevation 157 during attachment of the cap 120.

Figure 24:
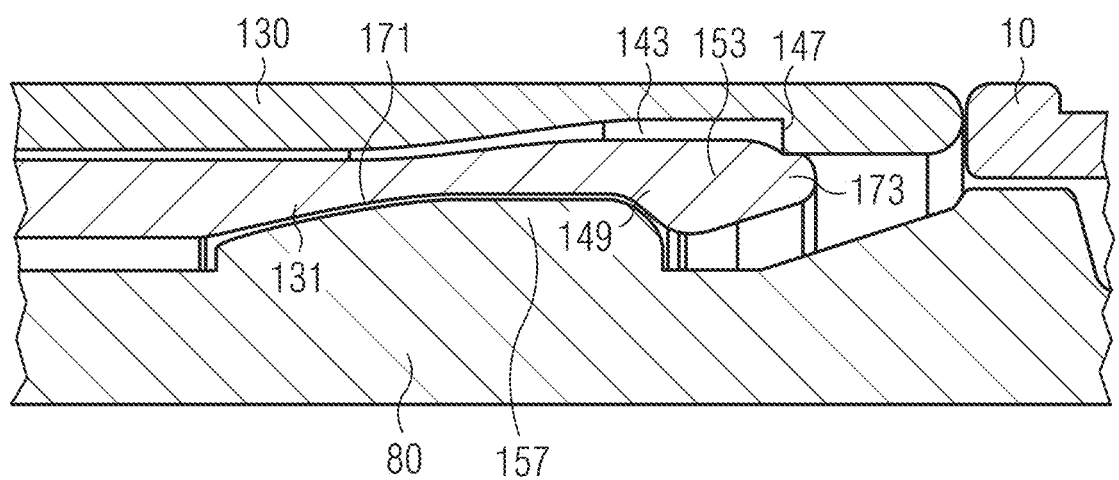
FIG. 24 shows a sectional view of the proximal section of the cap after attachment.

FIG. 24 shows a sectional view of the proximal section of the cap 120 after attachment to the drug delivery device 1.

The internal bump feature 153 is engaged behind the proximal edge of the elevation 157. The elevation 157 engages to the cavity 171 of the inner cap element 131. Though the internal bump feature 153 has slid over the elevation 157, the cap snap feature 149 is still deformed into the cavity 143 of the outer cap element 130. The combination of the proximal edge 147 of the outer cap element 130 holding the proximal end 173 of the cap snap means 149 in its position and the elevation 157 pushing the deformable region 151 into the cavity 143 of the outer cap element 130 cause a close or interference fit of the cap snap feature 149 over the elevation 157, thereby holding the cap 120 in the attached position.

Figure 25:
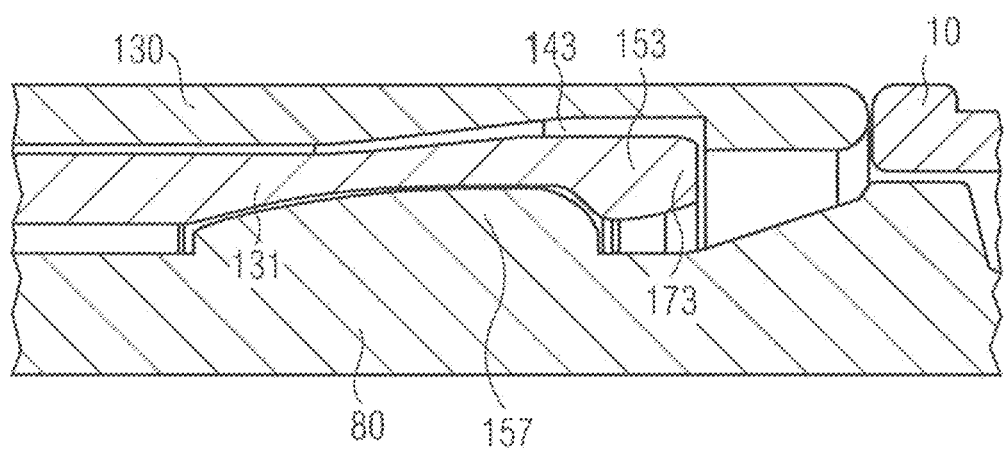
FIG. 25 shows a sectional view of the proximal section of an alternative embodiment of the cap after attachment.

FIG. 25 shows a sectional view of the proximal section of another embodiment of cap 120 after attachment to the drug delivery device 1.

This embodiment differs from the one described above by the design of the inner cap element 131. The proximal end 173 of the cap snap means 149 does not extend over the proximal edge of the cavity 143, which allows a deformation in such a manner that the proximal edge 173 also moves into to the cavity 143 during attachment. In this embodiment the cap snap means 149 are able to deform more readily with less force input required from the elevation 157.

The features of the embodiments mentioned above may be combined. The layout, function, and number of components may be changed in other embodiments.

In the following, the clip element 134 is described in more detail with reference to FIGS. 26 to 39.

Figure 26:
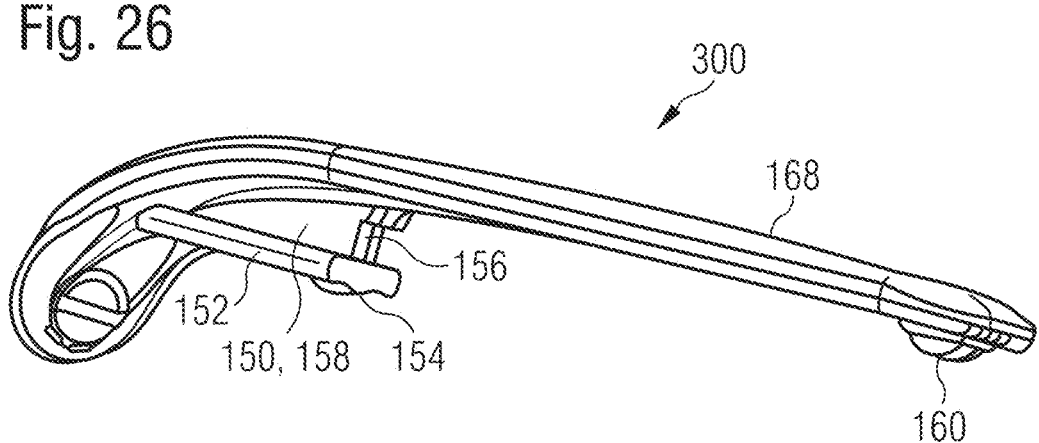
FIG. 26 shows a perspective view of a first component of a clip element.
Figure 32:
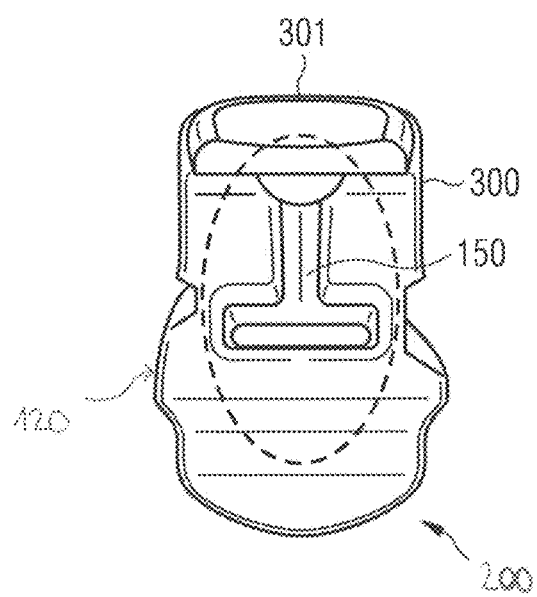
FIG. 32 shows a perspective view of a cap assembly.

FIGS. 26 and 32 show the clip element 134 or fixing element of the drug delivery device 1. By means of the clip element 134, a fixation or attachment of a cap, e.g. the previously described cap 120, or a cap assembly 200 (see below) of the drug delivery device 1 or the drug delivery device 1 may be fixed to a further component. The clip element 134 comprises a fixing portion 168 or main body with an elongate shape (see FIG. 31). Moreover, the clip element 134 comprises a slight curvature at a distal end (left in FIG. 26) of the clip element 134.

The clip element 134 comprises two components, i.e. a first component 300 and a second component 301 (see FIGS. 31 to 38, for example). Each one of the first and the second component 300, 301 is integrally formed. This may mean that the first and the second component 300, 301 are single-piece components. The first and the second component 300, 301 are attached, preferably non-releasably attached, to one another. The second component 301 is adapted and arranged to at least partly receive the first component 300. In particular, the first component 300 is at least partly introduced into the second component 301. Thus, the second component 301 may provide an outer shell of the clip element 134.

The first component 300 is at least in parts flexible and/or elastically deformable. In particular, the first component 300 comprises a flexible section. The flexible section provides a local radial flexibility of the first component 300 enabling the attachment of the clip element 134 to a further component, e.g. a jacket pocket. The first component 300 comprises plastic. In particular, the first component 300 is a plastic component. This may provide a certain degree of elastic deformability of the first component 300 per se. The first component 300 is injection moulded, for example.

In section, the first component 300 is shaped I-like (see, for example, FIG. 37). One horizontal stroke or bar of the "I" may, thereby, at least in parts be received by the second component 301 (upper horizontal stroke in FIG. 37). In the following, this stroke is referred to as "the upper horizontal stroke". The upper horizontal stroke may constitute the previously mentioned main body or elongated body 168. A further horizontal stroke or bar of the "I" may be received by the previously mentioned cap 120, which is described later on in more detail. A vertical stroke or bar of the "I" may connect the two horizontal strokes.

The first component 300 comprises a tip 303 (see FIGS. 38 and 39, for example). The tip 303 is arranged in a proximal end section of the clip element 134. The tip 303 may constitute the very proximal region of the first component 300. In particular, the tip 303 may constitute the proximal end of the upper stroke of the "I".

In the proximal end section, a thickness or radial extension of the first component 300 reduces towards its very proximal end. Accordingly, the tip 303 comprises a reduced thickness as compared to further sections of the first component 300, e.g. a distal section or a middle section. In other words, the tip 303 is thinner or has a reduced radial extension as compared to the remainder of the first component 300. On an upper side of the tip 303, i.e. that side, which faces the second component 301, the tip 303 may be slightly sloped. The thin tip 303 enables the first component 300 to flex locally in this region, as mentioned above.

The second component 301 may be made of a rigid material. In particular, the second component 301 may comprise a material which is more rigid than the material of the first component 300. The second component 301 may comprise metal, e.g. steel. The second component 301 may completely consist of metal. In this embodiment, the second component 301 may be stamped from a sheet of metal and then plated. In an alternative embodiment, the second component 301 may comprise fibreglass. The second component 301 may completely consist of fibreglass.

The second component 301 comprises an elongate shape having rounded edges. The second component 301 comprises a shape which is adjusted to the shape of an upper side of the first component 300 such that the second component can at least partly receive and/or cover the first component 300. The second component 301 comprises folded over edges or side walls. The folded over side walls may comprise a radial extension or height similar or equal to a thickness of one of the horizontal strokes of the previously described "I" (see FIG. 37). The second component 301 further comprises a curvature in a distal end section. By means of the rigid and hard material of the second component 301, a high quality and hard-wearing exterior surface of the clip element 134 is provided. In the embodiment where the second component 301 comprises metal, the second component 301 can further be given a variety of metallic colours.

The second component 301 further comprises a cavity or clearance region 304 (see FIG. 39). The cavity 304 is arranged on the underside of the second component 301, i.e. that side of the second component 301 which faces the first component 300 when the components 300, 301 are attached to one another. The cavity 304 is delimited by the folded over side walls. The design of the tip 303 allows it to flex into the cavity 304 of the second component 301, thus replicating a pinching effect of a standard pocket clip. In this way, a measure of retention is provided when the cap 120 and, hence, the device 1 is placed into a pocket or similar.

The first and second component 300, 301 are firmly connected to one another. Preferably, the first and the second component 300, 301 are non-releasably connected to one another. The second component 301 is press fitted to or clipped onto the first component 300. In particular, the second component 301 is press-fitted over the first component 300, thus providing a robust and hard-wearing shell for the first component 300.

Figure 33:
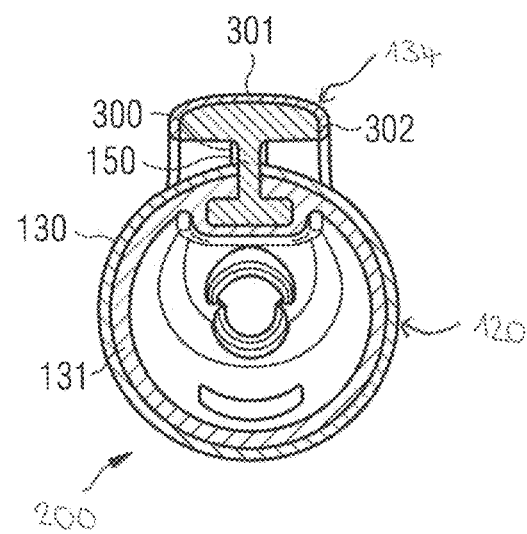
FIG. 33 shows a sectional view of the cap assembly of FIG. 32.
Figure 34:
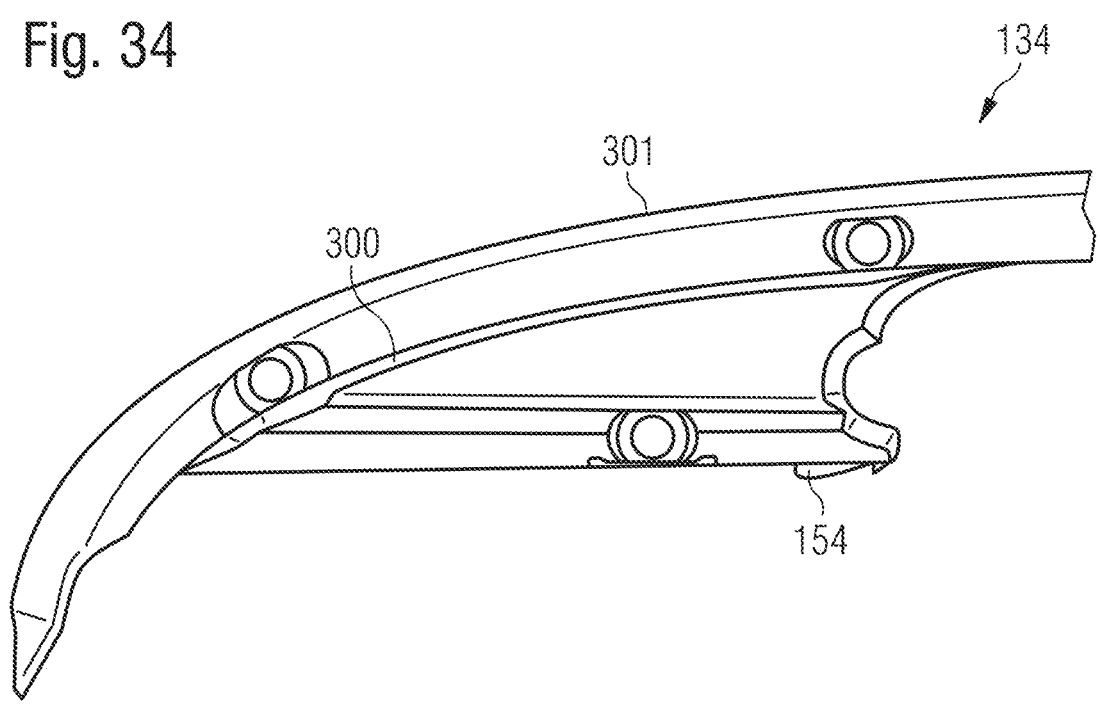
FIG. 34 shows a distal portion of a clip element.

The second component 301 comprises a retaining feature 302, which is shown in FIGS. 33, 36 and 37, for example. The retaining feature 302 may extend along the whole length of the second component 301. The retaining feature 302 may comprise the previously mentioned side walls of the second component 301. The fold over of the respective side wall is greater than 90 degrees with respect to a lateral axis of the clip element 134. The fold over may be 91, 92, 93, 94, 95, 100 or 105 degrees, for example. The folded over side walls do not contact an underside of the second component 301, wherein the underside may be that side of the second component 301 facing and/or receiving the first component 300 when the clip element 134 is assembled.

The folded over side walls of the second component 301 delimit an inner space of the second component in which the first component 300 is partly received when assembling the clip element 134. For coupling the first component 300 and the second component 301 to one another, in particular for clipping the second component 301 onto the first component 300, the first component 300 is partly or wholly introduced into the second component 301. An upper side of the first component 300 is received between the folded over side walls of the second component 301. In particular, the upper horizontal stroke of the "I"-shaped first component 300 is introduced over its whole length between the folded over side walls 302 of the second component 301. The folded over side walls of the second component 301 thereby keep the first component 300 in a predefined position with respect to the second component 301. The design of the components 300, 301 allows for an elastic deformation especially of the second component 301 when the first component 300 is inserted past the folded over side walls. The second component 301 forms a C-section when viewed in cross section (see FIGS. 36 and 37). This allows a relatively large amount of flexibility of the tips of the 'C', when the second component 301 is clipped onto the first component 300. The first component 300 acts as a solid block in compression. Once inserted, the second component 301 may spring back for retention. Due to the fold over of the side walls being just greater than 90 degrees, the second component 301 is firmly retained once press-fitted over the first component 300.

However, preferably before the second component 301 and the first component 300 are connected to one another as described above, the first component 300 of the clip element 134 is secured to the cap 120. For securing the clip element 134 and, in particular the first component 300, to the cap 120, the first component 300, comprises a guiding element 150, which can be seen from FIGS. 26 and 31, for example. The guiding element 150 is disposed in a distal end section of the first component 300 at an inside of the above mentioned curvature. The guiding element 150 is arranged on an underside of the first component 300 facing away from the second component 301. The guiding element 150 may constitute or comprise a rail such that the clip element 134 may be guided by an element receiving the guiding element 150, preferably, along a longitudinal axis of the clip element 134 or the device 1.

The guiding element 150 extends over less than half of the axial extension of the first component 300 of the clip element 134. The guiding element 150 comprises a T-shaped cross-section for facilitating the mentioned guiding functionality (see also FIG. 29). In order to form the T-shaped section, the guiding element 150 comprises a receiving portion 152 (see FIG. 26). The receiving portion 152 may constitute the horizontal stroke or bar of the "T" of the T-shaped section. Preferably, the receiving portion 152 is configured to be received by one or more openings or apertures of the components to which the clip element 134 is to be mounted, e.g. in a cap assembly 200 (see FIGS. 29 and 30).

Furthermore, the guiding element 150 comprises a guiding portion 158 (see FIG. 26). The guiding portion 158 constitutes the vertical stroke or bar of the "T" of the T-shaped section of the guiding element 150. The guiding portion 158 may be a web connecting the elongated main body (upper horizontal stroke of the "I") of the first component 130 with the receiving portion 152. The guiding portion 158 may further be received by or arranged in one or more openings of the components to which the clip element 134 is to be mounted, e.g. in the mentioned cap assembly 200.

The guiding element 150 comprises a connection feature 154. The connection feature 154 comprises or constitutes a protrusion protruding radially at the underside of the first component 130. Preferably, the connection feature 154 is configured to interact with a corresponding connection feature 170, e.g. of an inner part 131 (see FIG. 28) for connecting the first component 300 and the cap 120. The connection feature 154 is disposed in a proximal end section of the guiding element 150. The connection feature 154 may further comprise or constitute a distal face of the guiding element 150.

The first component 300 further comprises a feature 156. The feature 156 comprises a radial face with a normal perpendicular to the longitudinal axis (not explicitly indicated) of the first component 300 and a longitudinal face which is designed to hide or cover over any gaps between the first component 300 of the clip element 134 and the outer part 130 resulting from tolerances in manufacture and assembly. The feature 156 is designed to be in small amount of clearance rather than abutting in nominal tolerance conditions. In particular, the feature 156 may be configured to be in small amount of clearance to one or more corresponding components to which the clip element 134 is to be mounted, e.g. in the cap assembly 200 (see FIG. 30).

The specific type of connection between the first component 300 of the clip element 134 and the cap 120 can, of course, be varied. That is to say, the specific connection between the first component 300 and the cap 120 can be realized differently than with the guiding element 150 which comprises the connection feature 154, where the proposed connection does, of course, have advantages. However, disregarding the specific connection between the first component 300 and the cap 120, in the present context, the second component 301 of the clip element 134 may be attached to the cap only indirectly, that is to say without an immediate connection or even without any mechanical contact between the cap and the second component.

Moreover, the clip element 134, in particular the first component 300, comprises an attachment feature 160. The attachment feature 160 may be configured to interact with a further component (see depression 166 in FIG. 27). The attachment feature 160 comprises a bump. The attachment feature 160 is axially spaced from the guiding element 150 and arranged near a proximal end of the first component 300. The attachment feature is arranged on the underside of the first component 300 facing away from the second component 301. The attachment feature 160 is, preferably, configured to interact with the outer part 130 by means of mechanical contact, or close proximity to create a 'pinch point'. Thereby, fixation or attachment of the cap assembly 200 or drug delivery device 1 to the further element, such as a shirt pocket of a user of the assembly 200 or the device 1 may be facilitated or aided. Particularly, said mechanical contact may increase friction and, therewith, the reliability of the attachment of the cap assembly 200 and the further element.

Figure 27:
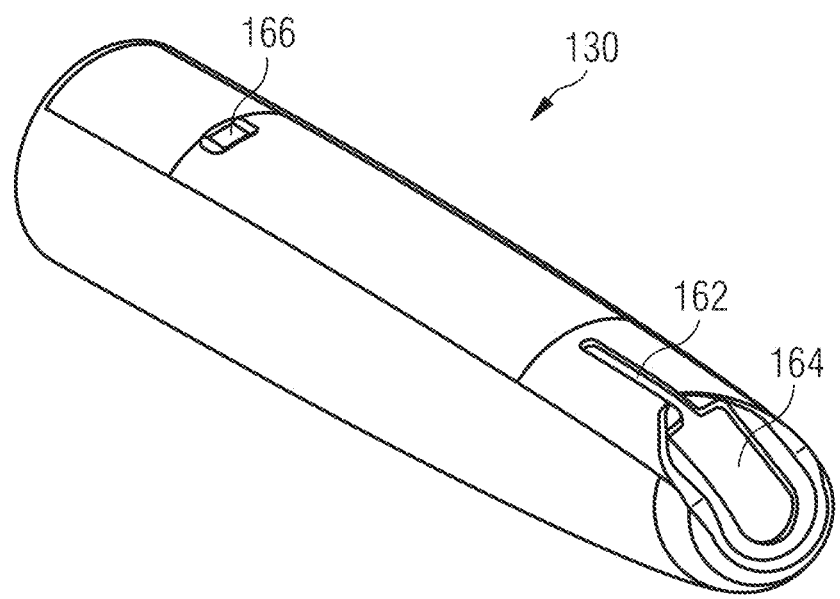
FIG. 27 shows a perspective view of an outer component.

FIG. 27 shows a perspective view of an outer part 130 which may be or relate to the above-mentioned outer cap element. The outer part 130 comprises an elongate shape. The outer part 130 further comprises a sleeve-like shape. Preferably, the outer part 130 is made of a metal, e.g. from aluminum. To this effect, the outer part 130 is, preferably, formed or fabricated by deep drawing (as mentioned above). The outer part 130 further comprises the previously mentioned opening 164. The opening 164 is arranged at a distal end of the outer part 130. The opening 164 is, preferably, formed from the outer part 130 by punching. The outer part 130 may further comprise a proximal opening which is not explicitly indicated in FIG. 27. Formed within the opening 164 is a corresponding guiding feature 162 corresponding to the guiding element 150 described by means of FIG. 26. The corresponding guiding feature 162 extends—originating from the opening 164—in a proximal direction of the outer part 130. The corresponding guiding feature 162 may be a guide slot. The corresponding guiding feature 162 may be configured to receive the guiding portion 158 of the guiding element 150 such that the guiding portion 158 is arranged inside the corresponding guiding feature 162. Preferably, the opening 164, the corresponding guiding feature 162 and the clip element 134 are configured such that the guiding element 150 can be introduced in or received by the opening 164. When then—e.g. during an assembly of the cap assembly 200—the first component 300 is pushed proximally, the guiding portion 158 may be received by or arranged in the corresponding guiding feature 162, wherein the receiving portion 152 is, preferably, only received by the remainder of the opening 164 and arranged inside the outer part 130 and/or the inner part 131 (see FIGS. 29 and 30).

The outer part 130 further comprises the previously mentioned depression 166. The depression 166 receives or interacts with the above-mentioned attachment feature 160 of the clip element 134 when, e.g., the first component 300 and the outer part 130 are assembled (see FIGS. 29 and 30 below). Preferably, the attachment feature 160 extends into the depression 166 and/or contacts the outer part 130 in the depression 166. The depression 166 is axially, particularly proximally, spaced from the opening 164 along a longitudinal axis of the outer part 130. Preferably, the depression 166 is shaped according to the attachment feature 160, i.e. with similar curvature as the mentioned bump of the attachment feature 160 (see FIG. 26).

Figure 28:
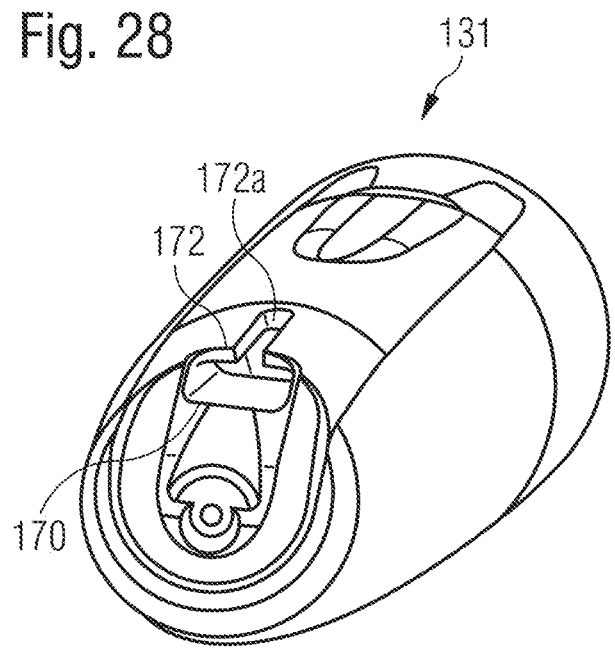
FIG. 28 shows a perspective view of an inner component.

FIG. 28 shows a perspective top view of an inner part 131. The inner part 131 may be a sleeve and configured to be introduced in the outer part 130. The inner part 131 comprises a corresponding connection feature 170. The corresponding connection feature 170 corresponds to the connection feature 154 of the first component 300 such that the first component 300 can be connected to the inner part 131 by an interaction of the connection feature 154 and the corresponding connection feature 170 (see FIG. 30). The corresponding connection feature 170 may constitute or comprise a proximal face of the inner part 131. The inner part 131 further comprises an opening 172. The opening 172 is arranged at or near the distal end of the inner part 131. The opening 172 may further be shaped similar to the opening 164 of the outer part (see FIG. 27). Formed within the opening 172 is a corresponding guiding feature 172a corresponding to the guiding element 150.

Figure 29:
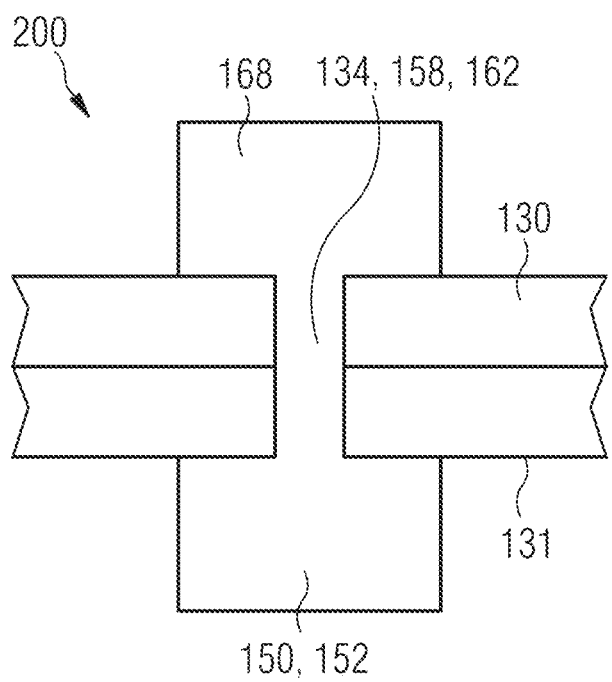
FIG. 29 shows a schematic cross-sectional view of parts of a cap assembly.
Figure 30:
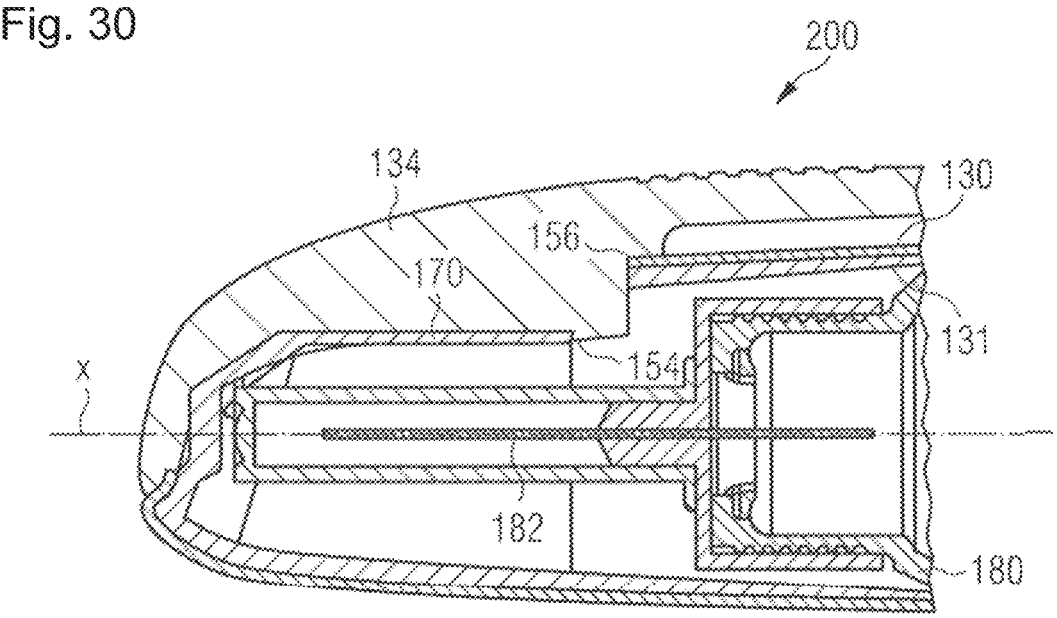
FIG. 30 shows a portion of the cap assembly in a longitudinal section.
Figure 31:
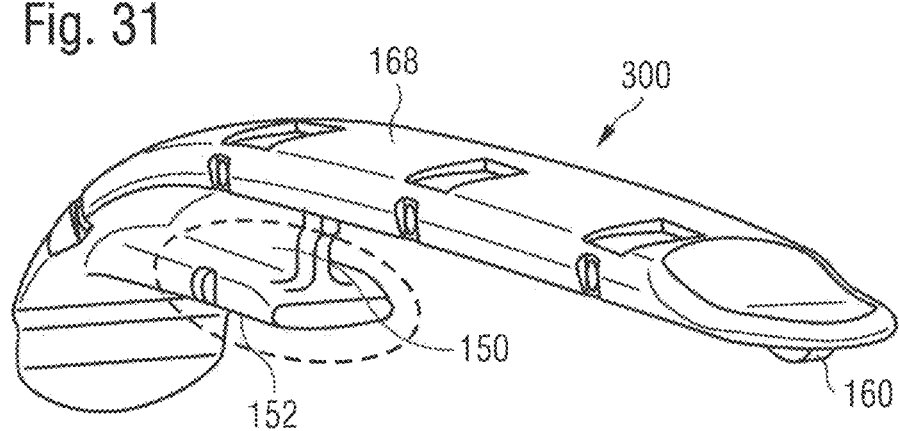
FIG. 31 shows a perspective view of a first component of a clip element.

FIG. 29 shows a schematic section of parts of a cap assembly 200 (see also FIG. 30). The assembly 200 comprises the previously described clip element 134 and the cap 120, in particular the outer part 130 and the inner part 131. FIG. 29 shows the mentioned components in an assembled state. An inner side of the cap assembly 200 is shown at the bottom and an outer part is shown at the top of the section shown in FIG. 29. In the depicted situation, the inner part 131 is arranged in the outer part 130 and at least a section of the clip element 134 and/or the guiding element 150 extends through the opening 164 of the outer part 130 and, preferably, also through the opening 172 of the inner part 131. To this effect, the openings 164 and 172 may overlap in the cap assembly 200. It is further shown in FIG. 29 that the guiding element 150 comprises the T-shaped section (said "T" is depicted upside down), as described above. The section of the whole first component 300 may, thereby, be shaped I-like, as described above. The guiding portion 158 is arranged in the corresponding guiding feature 162 (see also FIG. 29). The guiding element 150, particularly the receiving portion 152 may prevent an (outward) radial movement of the clip element 134 with respect to the outer part 130 and/or the inner part 131, for example. This is because the corresponding guiding feature 162 is too narrow, as to allow for the receiving portion 152 to radially pass or move through the corresponding guiding feature 162.

FIG. 30 shows a longitudinal section of parts of the cap assembly 200. The cap assembly 200 comprises a longitudinal axis X. The longitudinal axis X may coincide with the longitudinal axes of the clip element 134, the outer part 130 and the inner part 131. Also, a drug delivery device in which the cap assembly 200 is applied may be shown in FIG. 30.

The clip element 134 closes the opening 172 of the inner part 131 and the opening 164 of the outer part 130 such that a rounded shape of the cap assembly 200 results. The connection feature 154 is arranged at least partly in the opening 164 of the outer part 130, as well as in the opening 172 of the inner part 131 (openings are not explicitly indicated in FIG. 30).

Particularly, the corresponding guiding feature 162 is configured to receive the receiving portion 152 of the guiding element 150 such that the receiving portion 152 is arranged inside of the outer part 130 and also inside the inner part 131.

The clip element 134, in particular its first component 300, and the inner part 131 are connected with one another. Particularly, the connection feature 154 interacts with, preferably abuts, the corresponding connection feature 170 via a snap interaction such that the clip element 134, in particular the first component 300, and the inner part 131 are connected with respect to one another. The clip element 134 and the inner part 131 are, preferably, reliably connected to one another, as the distal face of the connection feature 154 and the proximal face of the corresponding connection feature 170 abut. In order to connect the mentioned components or during the connection, at least one of the first component 300 and the inner part 131, may at least slightly be deformed. The connection feature 154 blocks proximal movement (i.e. to the right in FIG. 30) of the inner part 131 with respect to the outer part 130 such that the inner part 131 is retained within the outer part 130.

The previously mentioned feature 156 is—under nominal tolerance conditions—arranged in a small amount of clearance to a distal face of the inner part 131 and a distal face and a radial face of the outer part 130 (faces are not explicitly indicated). Although this is not explicitly indicated in FIG. 30, the attachment feature 160 of the clip element 134, preferably, mechanically contacts or lies in close proximity to the depression 166 of the outer part 130 (see description above).

Also further components e.g. of a drug delivery device, wherein the cap assembly 200 may be applied to, are shown. Such components relate to a cartridge or cartridge holder 180 which may retain a drug (not explicitly indicated). Furthermore, an injection needle 182 is shown which is in fluid communication with the drug from the cartridge or cartridge holder 180. It is shown that the inner part 131 accommodates the needle 182, an inner needle cover and furthermore at least a section of the cartridge or cartridge holder 180.

The inner part may, advantageously, be designed to be mouldable by an injection moulding process with simple open-shut injection mould tooling. Thereby, it can be manufactured by a low-cost moulding process.

The cap 120 (see FIG. 3) may be or relate to the cap assembly 200.

The cartridge or cartridge holder 180 may be or relate to the cartridge 81 and/or to the cartridge holder 80.

The metal element of the cap may be or relate to the outer part 130.

The plastic element of the cap may be or relate to the inner part 131.

The outer cap element may be or relate to the outer part 130.

The inner cap element may be or relate to the outer part 131.

The aperture 135 may be or relate to the opening 164.

The scope of protection is not limited to the examples given herein above. The disclosure is embodied in each novel characteristic and each combination of characteristics, which particularly includes every combination of any features which are stated in the claims, even if this feature or this combination of features is not explicitly stated in the claims or in the examples.

REFERENCE NUMERALS 1 drug delivery device
10 outer housing part
11 distal part
12 rotational hard stop/stop features/second rotational stop
13 aperture
20 inner body/housing
21 external thread
22 splines
23 bayonet features
24 window retention nose/retaining means
25 stop faces/first rotational stop
30 piston rod
31 bearing
32 external thread/first outer thread
33 external thread/second outer thread
40 driver
41 distal driver part/separate components/distal portion/first component
42 proximal driver part/separate components/proximal portion/second component
43 coupler
44 external thread/helical groove
45 stop faces
46 splines
47 teeth features
48 fingers/flexible arms
49 bearing surface
50 dose nut
51 stop faces
52 external ribs
53 internal thread
60 display member
61 number sleeve/first component
62 dial sleeve/other component
63 stop face
64 helical drive face/protruding thread
65 clutch features/teeth
66 bearing face/flange/contact features
67 opposite faces
68 ratchet arm/dispense clicker/clicker feature
70 button
71 ratchet teeth/dispense clicker/clicker teeth
72 end face
73 arms/fingers
74 snap features
80 cartridge holder
81 cartridge
82 bayonet connection
83 aperture
84 distal end
90 clutch
91 drive sleeve splines
92 clutch biasing teeth
93 snap apertures/snap features
94 splines
95 clutch teeth
100 clicker
101 distal clicker part/second toothed element
102 proximal clicker part/first toothed element
103 spring
104 splines
105, 106 clicker teeth
107 external splines
108 shaped splines
109 clutch biasing teeth
110 spring
120 cap
230 window
101 distal clicker part
102 proximal clicker part
130 outer part/metal element of cap/outer cap element
131 inner part/plastic element of cap/inner cap element
132 metal element of outer housing part
133 plastic element of outer housing part
134 fixing element/clip element
135 aperture of cap
136 aperture of outer housing part
137 end face (of cap)
141 proximal section
143 cavity
147 edge
149 cap snap means
151 deformable region
153 internal bump feature
155 cap retention feature
157 elevation
161 folded end
171 cavity
173 proximal end
150 guiding element
152 receiving portion
154 connection feature
156 feature
158 guiding portion
160 attachment feature
162 corresponding guiding feature
164 opening (outer part)
168 fixing portion
166 depression
170 corresponding connection feature
172 opening (inner part)
172a guiding feature
180 cartridge/cartridge holder
182 injection needle 200 cap assembly
300 first component
301 second component
302 retaining feature
303 tip
304 cavity/clearance region
X longitudinal axis

The invention claimed is:

1. A cap assembly for a drug delivery device comprising a cap, and
a clip element which is configured to be attached to the cap, the clip element comprising a first component comprising plastic, and a second component comprising metal or fiberglass, wherein the first component is at least partly received by the second component, wherein the first component and the second component are connected to one another, and wherein the second component is attached to the cap by the connection between the first component and the second component,
wherein the second component comprises at least one retaining feature extending along an entire length of the second component, the at least one retaining feature configured to retain the first component in a predefined position with respect to the second component.

2. The cap assembly according to claim 1, wherein the second component is press fitted to the first component.

3. The cap assembly according to claim 1, wherein the at least one retaining feature comprises folded over side walls, wherein the fold over associated with the folded over side walls is greater than 90 degrees with respect to a longitudinal axis of the clip element.

4. The cap assembly according to claim 1, wherein the first component comprises a flexible tip, wherein the flexible tip is adapted and arranged to flex into a cavity of the second component.

5. The cap assembly according to claim 1, wherein the first component comprises a first connection feature, and wherein the cap assembly further comprises
an outer part with an opening,
an inner part located inside of the outer part and comprising an inner connection feature,
wherein a section of the first component extends through the opening of the outer part such that the first component is connected to the inner part due to mechanical interaction of the first connection feature of the first component and the inner connection feature of the inner part.

6. The cap assembly according to claim 5, wherein the interaction between the first and inner connection features is a snap-interaction.

7. The cap assembly according to claim 5, wherein the clip element is configured such that the first connection feature blocks movement of the inner part with respect to the outer part such that the inner part is retained within the outer part.

8. The cap assembly according to claim 5, wherein the first component of the clip element comprises a guiding element comprising a T-shaped section and the outer part and/or the inner part comprises a corresponding guiding feature, wherein the guiding element and the corresponding guiding feature are configured to cooperate to prevent a radial movement of the clip element with respect to the outer part.

9. The cap assembly according to claim 5, wherein the first component of the clip element comprises an attachment feature and the outer part comprises a depression which is axially spaced from the opening, wherein the attachment feature is in contact with or in close proximity to the depression on the outer part.

10. The cap assembly according to claim 1, wherein the clip element is configured to attach the cap assembly to a further element.

11. A drug delivery device comprising the cap assembly of claim 1 and a cartridge holder, wherein a cartridge containing a drug is received in the cartridge holder.

12. The cap assembly according to claim 1, wherein the second component defines a surface of the clip element which faces away from an outer surface of the cap.

13. The cap assembly according to claim 1, wherein at least one the retaining feature extends along a longitudinal direction of the second component.

14. A method for assembling a cap assembly for a drug delivery device, the method comprising:
providing a cap,
providing a first component of a clip element, the first component comprising plastic,
providing a second component of the clip element, the second component comprising metal or fiberglass, wherein the second component comprises at least one retaining feature extending along an entire length of the second component,
connecting the first component to the cap,
clipping the second component onto the first component, wherein the second component elastically deforms when the second component is clipped onto the first component, wherein the at least one retaining feature is configured to retain the first component in a predefined position with respect to the second component.

15. A drug delivery device comprising:
a cap assembly comprising:
a cap, and
a clip element which is configured to be attached to the cap, the clip element comprising a first component and a second component, wherein the first component is at least partly received by the second component, wherein the first component and the second component are connected to one another, wherein the second component is attached to the cap by the connection between the first component and the second component,
wherein the second component comprises at least one retaining feature extending along an entire length of the second component, the at least one retaining feature configured to retain the first component in a predefined position with respect to the second component, and
a reservoir holder configured to receive a reservoir containing a drug.

16. The drug delivery device according to claim 15, wherein the second component defines a surface of the clip element which faces away from an outer surface of the cap.

17. The drug delivery device according to claim 15, wherein the reservoir containing the drug is received in the reservoir holder.

18. The drug delivery device according to claim 15, wherein the second component comprises metal.

19. The drug delivery device according to claim 15, wherein the second component comprises fiberglass.

20. The drug delivery device according to claim 15, wherein at least one the retaining feature extends along a longitudinal direction of the second component.

* * * * *

UNITED STATES PATENT AND TRADEMARK OFFICE
CERTIFICATE OF CORRECTION

PATENT NO. : 11,291,776 B2
APPLICATION NO. : 16/303458
DATED : April 5, 2022
INVENTOR(S) : Plumptre It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 387 days.

Signed and Sealed this
Thirty-first Day of January, 2023

Katherine Kelly Vidal
*Director of the United States Patent and Trademark Office*